United States Patent
Shelton, IV et al.

(10) Patent No.: US 10,835,218 B2
(45) Date of Patent: Nov. 17, 2020

(54) APPARATUS AND METHOD TO DETERMINE END OF LIFE OF BATTERY POWERED SURGICAL INSTRUMENT

(71) Applicant: ETHICON LLC, Guaynabo, PR (US)

(72) Inventors: Frederick E. Shelton, IV, Hillsboro, OH (US); David C. Yates, West Chester, OH (US); Jason L. Harris, Lebanon, OH (US); Michael J. Vendely, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 528 days.

(21) Appl. No.: 15/634,385

(22) Filed: Jun. 27, 2017

(65) Prior Publication Data

US 2018/0368821 A1    Dec. 27, 2018

(51) Int. Cl.
*A61B 17/00* (2006.01)
*H02J 7/00* (2006.01)
(Continued)

(52) U.S. Cl.
CPC .. *A61B 17/00234* (2013.01); *A61B 17/07207* (2013.01); *A61B 17/1155* (2013.01);
(Continued)

(58) Field of Classification Search
CPC .......... A61B 17/00234; A61B 17/1155; A61B 17/07207; A61B 2017/2927; A61B 2090/0807; A61B 2017/0046; A61B 2090/0803; A61B 90/98; A61B 2017/00017; A61B 2560/0266; A61B 2017/07285; A61B 2017/07271; A61B 2017/07257; A61B 2017/00734; A61B 2017/00477; A61B 2017/00464; A61B 2017/00398; A61B 2017/0023; A61B 2017/00119; A61B 2017/00084;
(Continued)

(56) References Cited

U.S. PATENT DOCUMENTS 5,955,869 A * 9/1999 Rathmann .......... G01R 31/3648
                                                    320/132
6,025,695 A *  2/2000 Friel ................. H01M 10/4257
                                                    112/130
(Continued)

FOREIGN PATENT DOCUMENTS

EP       3 064 150 A1    9/2016

OTHER PUBLICATIONS

U.S. Appl. No. 15/634,418, filed Jun. 27, 2017.
(Continued)

*Primary Examiner* — Christopher Koharski
*Assistant Examiner* — James Moss
(74) *Attorney, Agent, or Firm* — Frost Brown Todd LLC

(57) ABSTRACT

A surgical instrument includes a handle assembly, a power source coupled with the handle assembly, and a control circuit coupled with the handle assembly and the power source. The handle assembly, the power source, and the control circuit are configured to drive an end effector of a shaft assembly coupled with the handle assembly to perform an operation on tissue. The control circuit is configured to receive life deduction event data. The control circuit is configured to determine an end of life for the power source based on the life deduction event data.

20 Claims, 12 Drawing Sheets

(51) Int. Cl.
    *H01M 10/44*     (2006.01)
    *A61B 17/072*     (2006.01)
    *A61B 17/115*     (2006.01)
    *A61B 90/98*     (2016.01)
    *A61B 90/00*     (2016.01)
    *A61B 17/29*     (2006.01)

(52) U.S. Cl.
    CPC ............... *H01M 10/44* (2013.01); *H02J 7/00* (2013.01); *A61B 90/98* (2016.02); *A61B 2017/00017* (2013.01); *A61B 2017/0023* (2013.01); *A61B 2017/00039* (2013.01); *A61B 2017/0046* (2013.01); *A61B 2017/00084* (2013.01); *A61B 2017/00119* (2013.01); *A61B 2017/00398* (2013.01); *A61B 2017/00464* (2013.01); *A61B 2017/00477* (2013.01); *A61B 2017/00734* (2013.01); *A61B 2017/07257* (2013.01); *A61B 2017/07271* (2013.01); *A61B 2017/07285* (2013.01); *A61B 2017/2927* (2013.01); *A61B 2090/0803* (2016.02); *A61B 2090/0807* (2016.02); *A61B 2560/0266* (2013.01); *H01M 2220/30* (2013.01); *H02J 7/0045* (2013.01)

(58) Field of Classification Search
    CPC ........ A61B 2017/00039; H01M 10/44; H01M 2220/30; H02J 7/00; H02J 7/0045
    See application file for complete search history.

(56) References Cited

U.S. PATENT DOCUMENTS

| | | | |
|---|---|---|---|
| 6,545,448 B1 * | 4/2003 | Stanley | H01M 10/4257 320/132 |
| 6,783,524 B2 | 8/2004 | Anderson et al. | |
| 7,000,818 B2 | 2/2006 | Shelton, IV et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 9,072,535 B2 | 7/2015 | Shelton, IV et al. | |
| 9,186,142 B2 | 11/2015 | Fanelli et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 10,133,248 B2 | 11/2018 | Fitzsimmons et al. | |
| 10,159,483 B2 | 12/2018 | Beckman et al. | |
| 2011/0022032 A1 * | 1/2011 | Zemlok | A61B 17/07207 606/1 |
| 2012/0071796 A1 * | 3/2012 | Smith | A61B 17/320092 601/3 |
| 2014/0263541 A1 | 9/2014 | Leimbach et al. | |
| 2015/0272575 A1 | 10/2015 | Leimbach et al. | |
| 2015/0280384 A1 * | 10/2015 | Leimbach | B25F 3/00 227/175.1 |
| 2015/0280424 A1 * | 10/2015 | Leimbach | G05F 5/00 361/18 |
| 2016/0106424 A1 * | 4/2016 | Yates | H01M 2/342 227/175.1 |
| 2017/0086823 A1 | 3/2017 | Leimbach et al. | |

OTHER PUBLICATIONS

U.S. Appl. No. 15/634,436, filed Jun. 27, 2017.
U.S. Appl. No. 15/634,452, filed Jun. 27, 2017.
U.S. Appl. No. 15/634,475, filed Jun. 27, 2017.
U.S. Appl. No. 15/634,497, filed Jun. 27, 2017.
U.S. Appl. No. 15/634,524, filed Jun. 27, 2017.
U.S. Appl. No. 15/634,556, filed Jun. 27, 2017.
U.S. Appl. No. 15/634,589, filed Jun. 27, 2017.
U.S. Appl. No. 15/634,620, filed Jun. 27, 2017.
European Search Report, Extended, and Written Opinion dated Aug. 24, 2018 for Application No. EP 18180172.1, 8 pgs.
European Examination Report dated Aug. 22, 2019 for Application No. EP 18180172.1, 3 pgs.
International Search Report and Written Opinion dated Aug. 24, 2018 for Application No. PCT/IB2018/053665, 10 pgs.

* cited by examiner

APPARATUS AND METHOD TO DETERMINE END OF LIFE OF BATTERY POWERED SURGICAL INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in various ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,000,818, entitled "Surgical Stapling Instrument Having Separate Distinct Closing and Firing Systems," issued Feb. 21, 2006; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
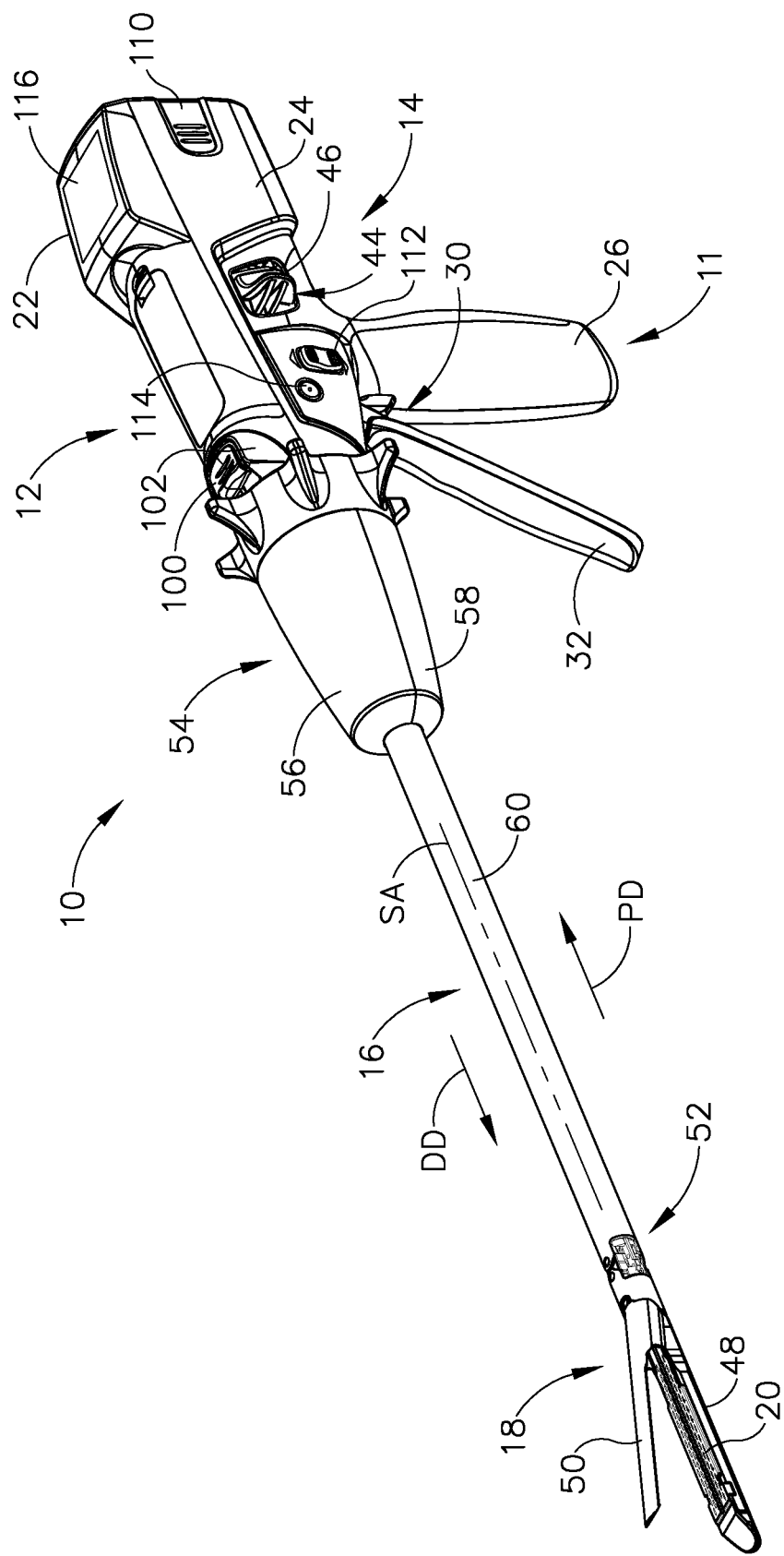
FIG. 1 depicts a perspective view of an exemplary surgical instrument including an interchangeable shaft assembly and a handle assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Although the surgical instruments described herein comprise motorized implements for cutting and stapling, it will be appreciated that the configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that includes a handle assembly (11) and a removable shaft assembly (16). In some versions, handle assembly (11) and shaft assembly (16) are each provided a single-use, disposable components. In some other versions, handle assembly (11) and shaft assembly (16) are each provided as reusable components. As another merely illustrative example, shaft assembly (16) may be provided as a single-use, disposable component while handle assembly is provided as a reusable component. Various suitable ways in which reusable versions of handle assembly (11) and shaft assembly (16) may be suitable reprocessed for reuse will be apparent to those of ordinary skill in the art in view of the teachings herein.

Handle assembly (11) of the present example includes a housing (12), a closure trigger (32), and a firing trigger (33). At least a portion of housing (12) forms a handle (14) that is configured to be grasped, manipulated and actuated by the clinician. Housing (12) is configured for operative attachment to shaft assembly (16), which has a surgical end effector (18) operatively coupled thereto. As described below, end effector (18) is configured to perform one or more surgical tasks or procedures. In particular, end effector (18) of the example shown in FIG. 1 is operable to perform a surgical cutting and stapling procedure, in a manner similar to an end effector of a conventional endocutter, though it should be understood that this is just one merely illustrative example.

Figure 2:
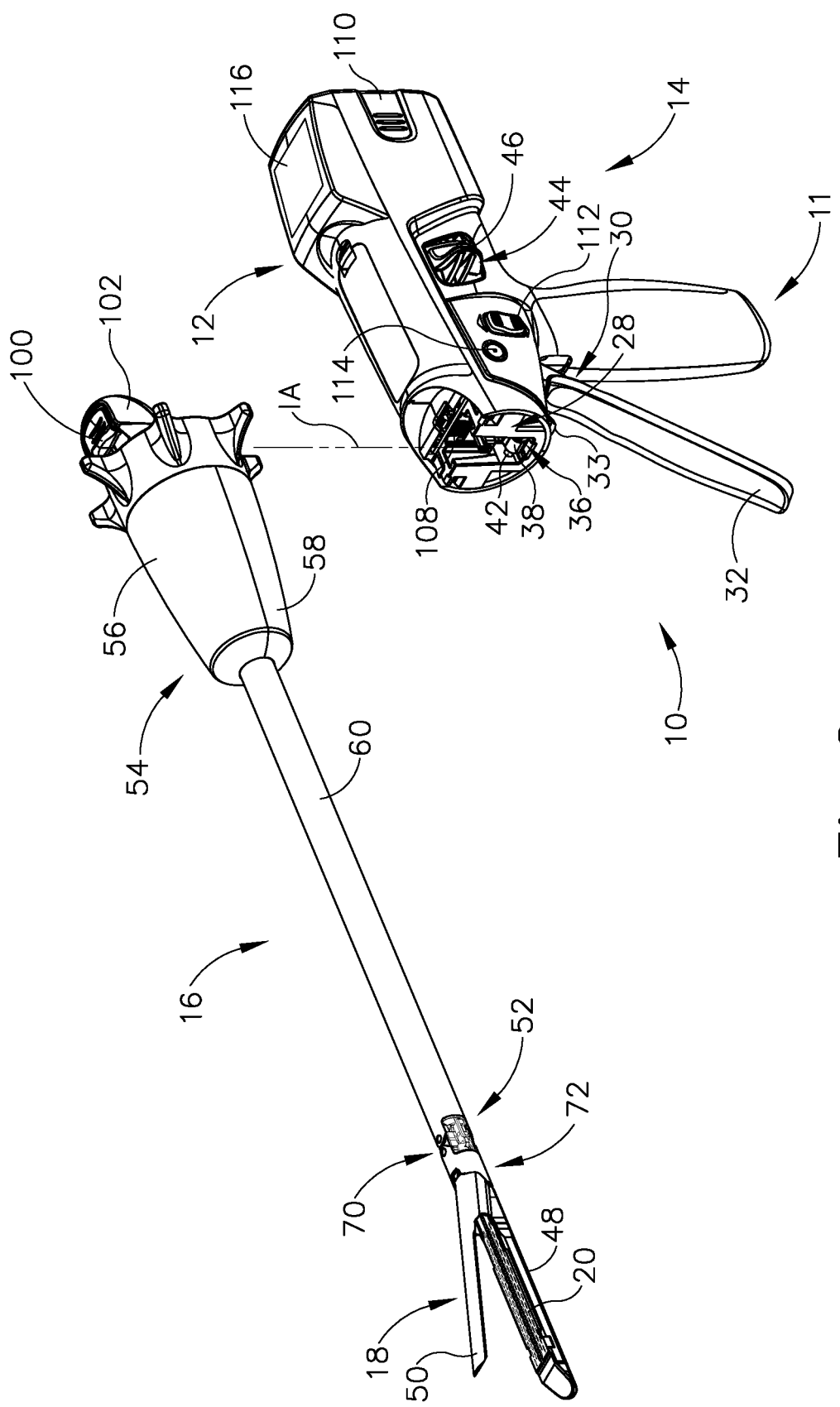
FIG. 2 depicts a perspective view of the instrument of FIG. 1, showing the shaft assembly disassembled from the handle assembly of the instrument.
Figure 3:
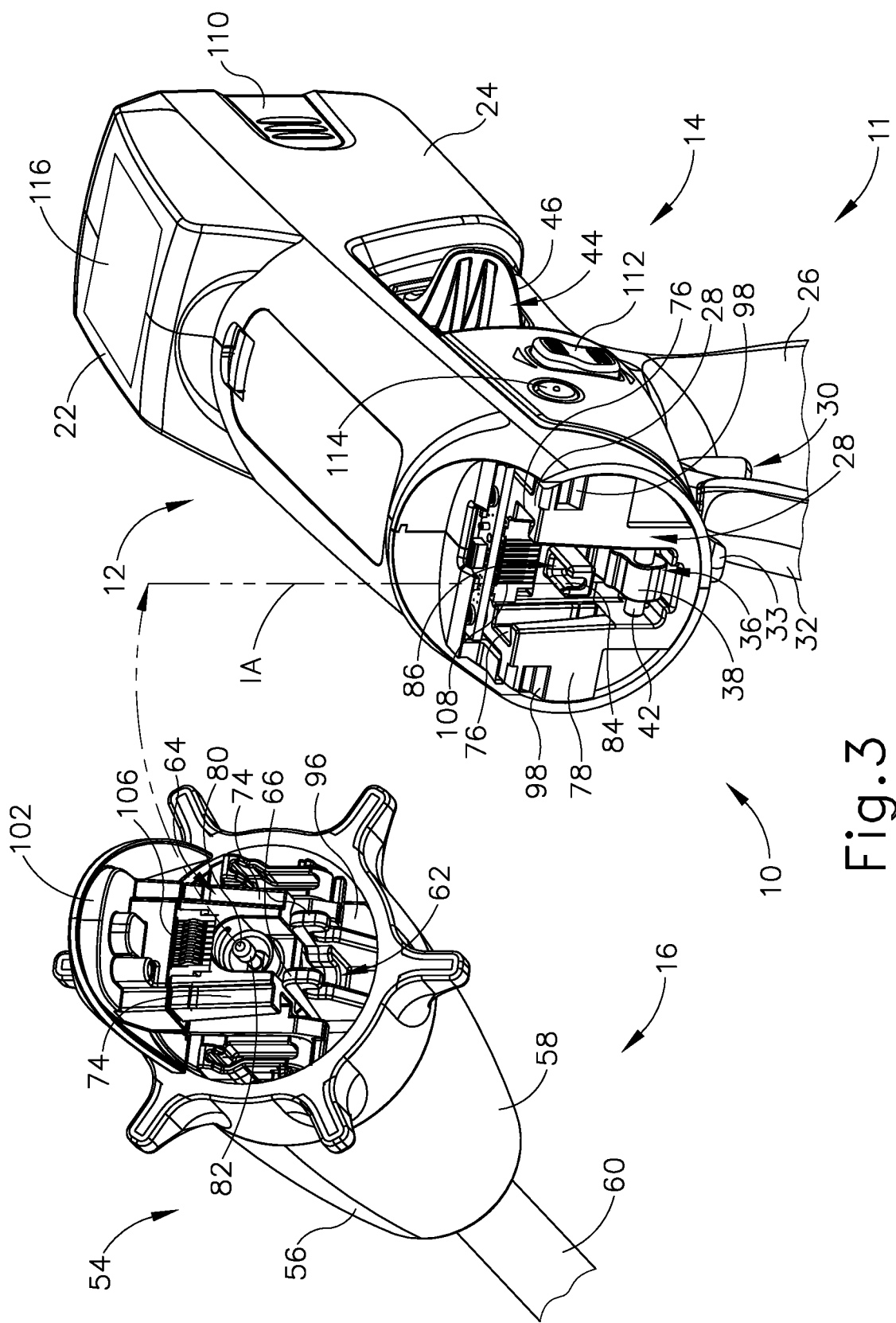
FIG. 3 depicts a partial perspective view of the instrument of FIG. 1, showing the shaft assembly disassembled from the handle assembly of the instrument.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be grasped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto. As will also be discussed in further detail below, triggers (32, 33) are pivotable toward pistol grip portion (26) to activate at least some of the drive systems in handle (14).

Figure 5:
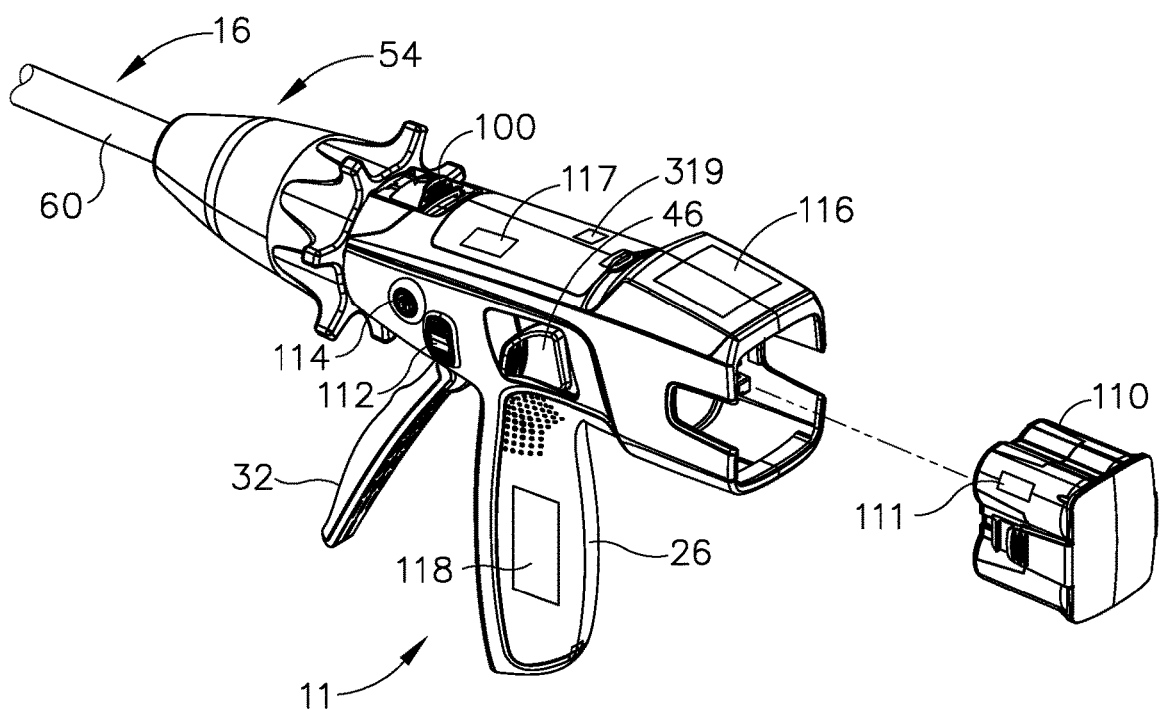
FIG. 5 depicts a perspective view of a proximal portion of the instrument of FIG. 1, with a battery removed from the handle assembly.

At least some of the drive systems in handle assembly (11) are ultimately driven by a motor (118), which is shown schematically in FIG. 5. In the present example, motor (118) is located in pistol grip portion (26), though it should be understood that motor (118) may be located at any other suitable position. Motor (118) receives power from a battery pack (110), which is secured to handle (14). In the present example, and as shown in FIG. 5, battery pack (110) is removable from handle (14). In some other versions, battery pack (110) is not removable from handle (14). In some such versions, battery pack (110) (or a variation thereof) is fully contained within handle housing segments (22, 24). Various suitable forms that motor (118) and battery pack (110) may take will be apparent to those of ordinary skill in the art in view of the teachings herein.

As also shown schematically in FIG. 5, a control circuit (117) is contained within handle (14). By way of example only, control circuit (117) may comprise a microcontroller and/or various other components as will be apparent to those of ordinary skill in the art in view of the teachings herein. Control circuit (117) is configured to store and execute control algorithms to drive motor (118). Control circuit (117) is also configured to drive a graphical user interface (116), which is located at the proximal end of handle assembly (11). In some versions, control circuit (117) is configured to receive and process one or more signals from shaft assembly (16). By way of example only, control circuit (117) may be configured and operable in accordance with at least some of the teachings of U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein. Other suitable ways in which control circuit (117) may be configured and operable will be apparent to those of ordinary skill in the art in view of the teachings herein.

As best seen in FIG. 3, a frame (28) of handle (14) operatively supports a plurality of drive systems. In this particular example, frame (28) operatively supports a "first" or closure drive system, generally designated as (30), which may be employed to apply closing and opening motions to interchangeable shaft assembly (16) that is operatively attached or coupled thereto. Also in this particular example, closure drive system (30) includes an actuator in the form of a closure trigger (32) that is pivotally supported by frame (28). More specifically, closure trigger (32) is pivotally coupled to housing (14) by a pin (not shown). Such arrangement enables closure trigger (32) to be manipulated by a clinician such that when the clinician grasps pistol grip portion (26) of handle (14), closure trigger (32) may be easily pivoted from a starting or "unactuated" position (FIG. 4A) toward pistol grip portion (26) to an "actuated" position; and more particularly to a fully compressed or fully actuated position (FIG. 4B). Closure trigger (32) may be biased into the unactuated position by spring or other biasing arrangement (not shown).

In the present example, closure drive system (30) further includes a closure linkage assembly (36) pivotally coupled to closure trigger (32). A portion of closure linkage assembly (36) is shown in FIG. 3. Closure linkage assembly (36) may include a first closure link (not shown) and a second closure link (38) that are pivotally coupled to closure trigger (32) by a pin (not shown). Second closure link (38) may also be referred to herein as an "attachment member" and includes a transverse attachment pin (42). As shown in FIG. 3, attachment pin (42) is exposed when shaft assembly (16) is detached from handle assembly (11). Attachment pin (42) may thus couple with a complementary feature of a shaft assembly (16) when shaft assembly (16) is coupled with handle assembly (11), as described in greater detail below.

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upwardly to a point where a locking pawl (not shown) drops into retaining engagement with first closure link (not shown), thereby preventing closure trigger (32) from returning to the unactuated position. Thus, closure release assembly (44) serves to lock closure trigger (32) in the fully actuated position.

When the clinician desires to unlock closure trigger (32) from the actuated position to return to the unactuated position, the clinician simply pivots closure release button assembly (46) by urging release button assembly (46) distally, such that locking pawl (not shown) is moved out of engagement with the first closure link (not shown). When the locking pawl (not shown) has been moved out of engagement with first closure link (not shown), closure trigger (32) may return back to the unactuated position in response to a resilient bias urging closure trigger (32) back to the unactuated position. Other closure trigger locking and release arrangements may also be employed.

Interchangeable shaft assembly (16) further includes an articulation joint (52) and an articulation lock (not shown) that can be configured to releasably hold end effector (18) in a desired position relative to a longitudinal axis of shaft assembly (16). In the present example, articulation joint (52) is configured to allow end effector (18) to be laterally deflected away from the longitudinal axis of shaft assembly (16), as is known in the art. By way of example only, end effector (18), articulation joint (52), and the articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned.

In the present example, articulation at articulation joint (52) is motorized via motor (118), based on control input from the operator via an articulation control rocker (112) on handle assembly (11). By way of example only, when the operator presses on the upper portion of articulation control rocker (112), end effector (18) may laterally pivot to the right (viewing instrument (10) from above) at articulation joint (52); and when the operator presses on the lower portion of articulation control rocker (112), end effector (18) may laterally pivot to the left (viewing instrument (10) from above) at articulation joint (52). In some versions, the other side of handle assembly (11) includes another articulation control rocker (112). In such versions, the articulation control rocker (112) on the other side of handle assembly (11) may be configured to provide pivoting of end effector (18) in directions opposite to those listed above in response to upper actuation of articulation control rocker (112) and lower actuation of articulation control rocker (112). By way of example only, articulation control rocker (112) and the rest of the features that provide motorized articulation of end effector (18) at articulation joint (52) may be configured and operable in accordance with at least some of the teachings of U.S. Pub. No. 2015/0280384, entitled "Surgical Instrument Comprising a Rotatable Shaft," published Oct. 1, 2015, issued as U.S. Pat. No. 10,201,364 on Feb. 12, 2019, the disclosure of which is incorporated by reference herein. Other suitable ways in which articulation control rocker (112) and the rest of the features that provide motorized articulation of end effector (18) at articulation joint (52) may be configured and operable will be apparent to those of ordinary skill in the art in view of the teachings herein.

End effector (18) of the present example comprises a lower jaw in the form of an elongated channel (48) that is configured to operatively a support staple cartridge (20) therein. End effector (18) of the present example further includes an upper jaw in the form of an anvil (50) that is pivotally supported relative to elongated channel (48). Interchangeable shaft assembly (16) further includes a proximal housing or nozzle (54) comprised of nozzle portions (56, 58); and a closure tube (60) that can be utilized to close and/or open anvil (50) of end effector (18). Shaft assembly (16) also includes a closure shuttle (62) that is slidably supported within a chassis (64) of shaft assembly (16) such that closure shuttle (62) may be axially moved relative to chassis (64). Closure shuttle (62) includes a pair of proximally-protruding hooks (66) that are configured for attachment to attachment pin (42) that is attached to second closure link (38). A proximal end (not shown) of closure tube (60) is coupled to closure shuttle (62) for relative rotation thereto, though the coupling of closure tube (60) with closure shuttle (62) provides that closure tube (60) and closure shuttle (62) will translate longitudinally with each other. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14).

In the present example, articulation joint (52) includes a double pivot closure sleeve assembly (70). Double pivot closure sleeve assembly (70) includes an end effector closure sleeve assembly (72) for engaging an opening tab on anvil (50) in the various manners described in U.S. Pub. No. 2014/0263541, now abandoned, the disclosure of which is incorporated by reference herein. It should be understood that double pivot closure sleeve assembly (70) is coupled with closure tube (60) such that double pivot closure sleeve assembly (70) translates with closure tube (60) in response to pivotal movement of closure trigger (32), even when articulation joint (52) is in an articulated state (i.e., when end effector (18) is pivotally deflected laterally away from the longitudinal axis of shaft assembly (16) at articulation joint (52)). Moreover, the engagement of end effector closure sleeve assembly (72) with anvil (50) provides pivotal movement of anvil (50) toward staple cartridge (20) in response to distal translation of double pivot closure sleeve assembly (70) and closure tube (60); and pivotal movement of anvil (50) away from staple cartridge (20) in response to proximal translation of double pivot closure sleeve assembly (70) and closure tube (60). While shaft assembly (16) of the present example includes articulation joint (52), other interchangeable shaft assemblies may lack articulation capabilities.

As shown in FIG. 3, chassis (64) includes a pair of tapered attachment portions (74) formed thereon that are adapted to be received within corresponding dovetail slots (76) formed within a distal attachment flange portion (78) of frame (28). Each dovetail slot (76) may be tapered or generally V-shaped to seatingly receive attachment portions (74) therein. A shaft attachment lug (80) is formed on the proximal end of an intermediate firing shaft (82). Thus, when interchangeable shaft assembly (16) is coupled to handle (14), shaft attachment lug (80) is received in a firing shaft attachment cradle (84) formed in a distal end of a longitudinal drive member (86). When shaft attachment lug (80) is received in firing shaft attachment cradle (84), intermediate firing shaft (82) will translate longitudinally with longitudinal drive member (86). When intermediate firing shaft (82) translates distally, intermediate firing shaft (82) actuates end effector (18) to drive staples into tissue and cut the tissue, as is known in the art. By way of example only, this actuation of end effector (18) may be carried out in accordance with at least some of the teachings of U.S. Pub. No. 2015/0280384, issued as U.S. Pat. No. 10,201,364 on Feb. 12, 2019, the disclosure of which is incorporated by reference herein; and/or in accordance with the teachings of various other references cited herein.

Figure 4A:
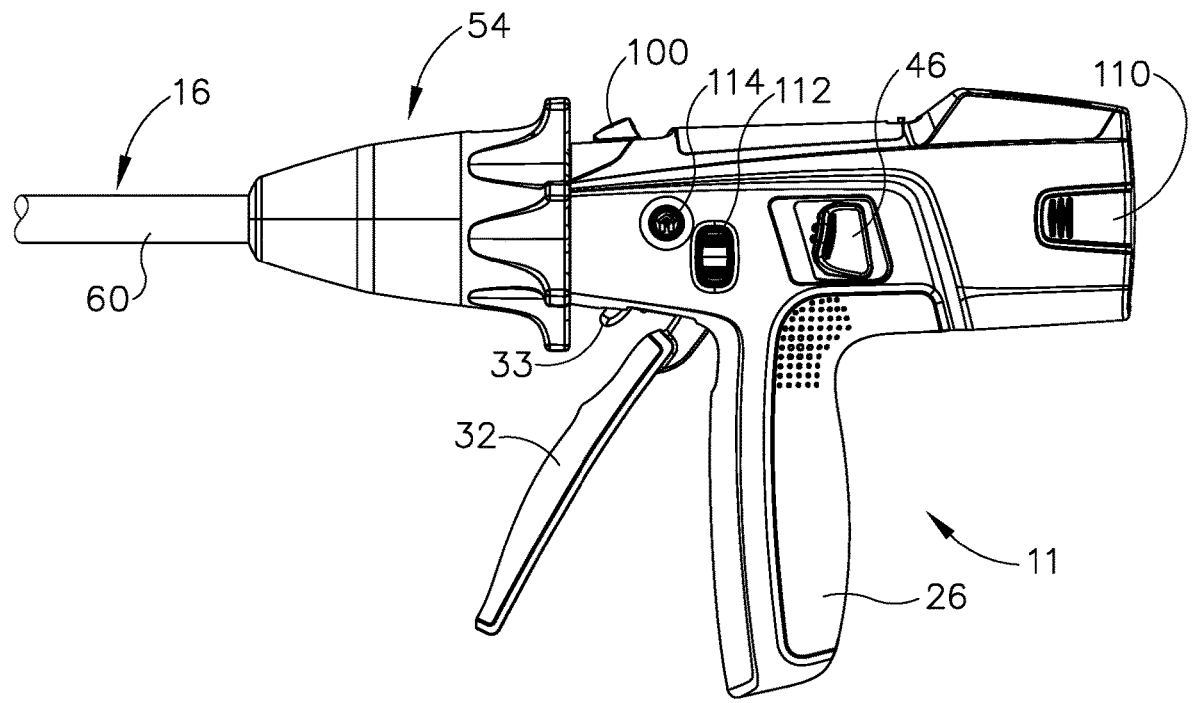
FIG. 4A depicts a side elevational view of a proximal portion of the instrument of FIG. 1, with a closure trigger in a first pivotal position and a firing trigger in a first pivotal position.
Figure 4B:
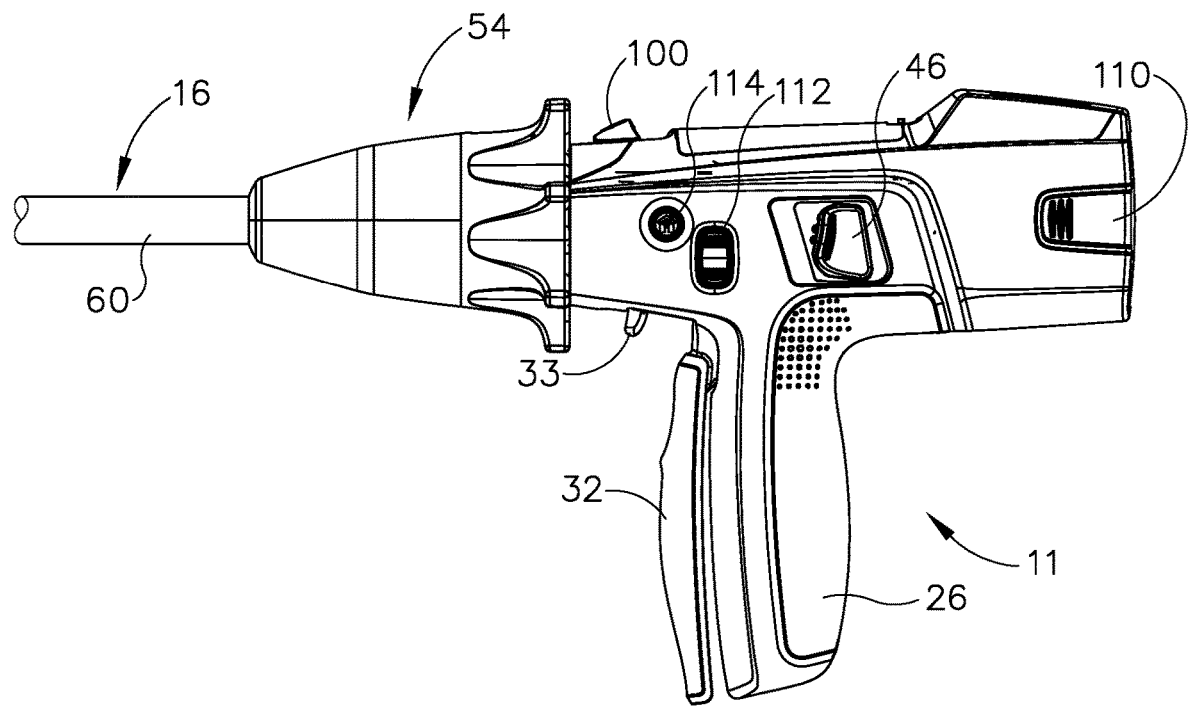
FIG. 4B depicts a side elevational view of a proximal portion of the instrument of FIG. 1, with the closure trigger in a second pivotal position and the firing trigger in a second pivotal position.
Figure 4C:
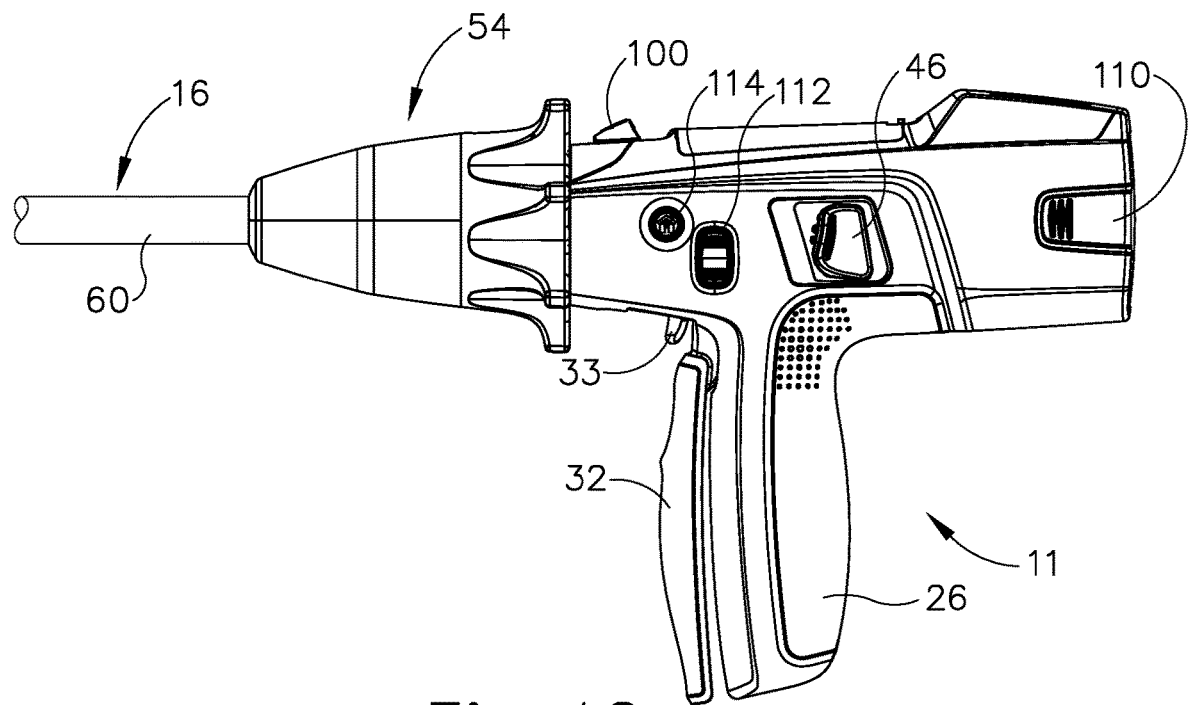
FIG. 4C depicts a side elevational view of a proximal portion of the instrument of FIG. 1, with the closure trigger in the second pivotal position and the firing trigger in a third pivotal position.

FIGS. 4A-4C show the different states of handle assembly (11) during the different states of actuation of end effector (18). In FIG. 4A, handle assembly (11) is in a state where closure trigger (32) is in a non-actuated pivotal position and firing trigger (33) is in a non-actuated pivotal position. At this stage, end effector (18) is in an opened state where anvil (50) is pivoted away from staple cartridge (20).

In FIG. 4B, handle assembly (11) is in a state where closure trigger (32) is in an actuated pivotal position. As noted above, closure trigger (32) will be locked in this position until the operator actuates release button assembly (46). At this stage, end effector is in a closed but unfired state where anvil (50) is pivoted toward staple cartridge (20), such that tissue is being compressed between anvil (50) and cartridge (20). However, firing shaft (82) has not yet been driven distally to actuate staples from staple cartridge (20), and the knife at the distal end of firing shaft (82) has not yet severed the tissue between anvil (20) and staple cartridge (20). It should be noted that firing trigger (33) is in a partially-actuated pivotal position in FIG. 4B, due to the travel of closure trigger (32) from the non-actuated pivotal position to the actuated pivotal position. However, this movement of firing trigger (33) is only provided in order to improve access to firing trigger (33) for the operator. In other words, this movement of firing trigger (33) from the position shown in FIG. 4A to the position shown in FIG. 4B does not yet activate a firing sequence.

In FIG. 4C, handle assembly is in a state where closure trigger (32) remains in the actuated pivotal position, and firing trigger (33) has been pivoted to an actuated pivotal position. This actuation of firing trigger (33) activates motor (118) to drive longitudinal drive member (86) longitudinally, which in turn drives firing shaft (82) longitudinally. The longitudinal movement of firing shaft (82) results in actuation of staples from staple cartridge (20) into the tissue compressed between anvil (50) and staple cartridge (20); and further results in the severing of the tissue compressed between anvil (50) and staple cartridge (20). In some versions, an additional safety trigger is provided. For instance, the additional safety trigger may prevent actuation of firing trigger (33) until the safety trigger is actuated. In other words, after reaching the state shown in FIG. 4B, when the operator is ready to actuate firing trigger (33), the operator must first actuate the safety trigger and then actuate firing trigger (33). It should be understood that the presence of a safety trigger may prevent inadvertent actuation of firing trigger (33).

It should also be understood that, in the present example, the actuation of anvil (50) toward staple cartridge (20) is provided through purely mechanical couplings between closure trigger (32) and anvil (50), such that motor (118) is not used to actuate anvil (50). It should also be understood that, in the present example, the actuation of firing shaft (82) (and, hence, the actuation of staple cartridge (20)) is provided through activation of motor (118). In addition, the actuation of articulation joint (52) is provided through activation of motor (118) in the present example. This motorized actuation of articulation joint (52) is provided via longitudinal translation of drive member (86). A clutch assembly (not shown) within shaft assembly (16) is operable to selectively couple longitudinal translation of drive member (86) with features to either drive articulation joint (52) or actuate staple cartridge (20). Such selective coupling via the clutch assembly is based on the pivotal position of closure trigger (32). In particular, when closure trigger (32) is in the non-actuated position shown in FIG. 4A, activation of motor (118) (in response to activation of articulation control rocker (112)) will drive articulation joint (52). When closure trigger (32) is in the actuated position shown in FIG. 4B, activation of motor (118) (in response to actuation of firing trigger (33)) will actuate staple cartridge (20). By way of example only, the clutch assembly may be configured and operable in accordance with at least some of the teachings of U.S. Pub. No. 2015/0280384, issued as U.S. Pat. No. 10,201,364 on Feb. 12, 2019, the disclosure of which is incorporated by reference herein.

In the present example, handle assembly (11) also includes a "home" button (114). By way of example only, when anvil (50) is in a closed position, "home" button (114) may be operable to activate motor (118) to retract drive member (86) proximally to a proximal-most, "home" position. In addition, or in the alternative, when anvil (50) is in an open position, "home" button (114) may be operable to activate motor (118) to drive articulation joint (52) to achieve a non-articulated state, such that end effector (18) is coaxially aligned with shaft assembly (16). In addition, or in the alternative, "home" button (114) may activate graphical user interface (116) to return to a "home" screen. Other suitable operations that may be provided in response to activation of "home" button (114) will be apparent to those of ordinary skill in the art in view of the teachings herein.

Shaft assembly (16) of the present example further includes a latch system for removably coupling shaft assembly (16) to handle assembly (11) and, more specifically, to frame (28). By way of example only, this latch system may include a lock yoke or other kind of lock member that is movably coupled to chassis (64). As shown in FIG. 3, such a lock yoke may include two proximally protruding lock lugs (96) that are configured for releasable engagement with corresponding lock detents or grooves (98) in frame (28). In some versions, the lock yoke is biased in the proximal direction by a resilient member (e.g., a spring, etc.). Actuation of the lock yoke may be accomplished by a latch button (100) that is slidably mounted on a latch actuator assembly (102) that is mounted to chassis (64). Latch button (100) may be biased in a proximal direction relative to the lock yoke. The lock yoke may be moved to an unlocked position by urging latch button (100) the in distal direction, which also causes the lock yoke to pivot out of retaining engagement with frame (28). When the lock yoke is in "retaining engagement" with frame (28), lock lugs (96) are retainingly seated within the corresponding lock detents or grooves (98). By way of further example only, shaft assembly (16) may be removably coupled with handle assembly (11) in accordance with at least some of the teachings of U.S. Pub. No. 2017/0086823, entitled "Surgical Stapling Instrument with Shaft Release, Powered Firing, and Powered Articulation," published Mar. 30, 2017, issued as U.S. Pat. No. 10,182,813 on Jan. 22, 2019, the disclosure of which is incorporated by reference herein; in accordance with at least some of the teachings of U.S. Pub. No. 2015/0280384, issued as U.S. Pat. No. 10,201,364 on Feb. 12, 2019, the disclosure of which is incorporated by reference herein; and/or in any other suitable fashion.

To commence the coupling process between shaft assembly (16) and handle assembly (11), the clinician may position chassis (64) of interchangeable shaft assembly (16) above or adjacent to frame (28) such that tapered attachment portions (74) formed on chassis (64) are aligned with dovetail slots (76) in frame (28). The clinician may then move shaft assembly (16) along an installation axis (IA) that is perpendicular to the longitudinal axis of shaft assembly (16) to seat attachment portions (74) in "operative engagement" with the corresponding dovetail receiving slots (76). In doing so, shaft attachment lug (80) on intermediate firing shaft (82) will also be seated in cradle (84) in the longitudinally movable drive member (86) and the portions of pin (42) on second closure link (38) will be seated in the corresponding hooks (66) in closure shuttle (62). As used herein, the term "operative engagement" in the context of two components means that the two components are sufficiently engaged with each other so that upon application of an actuation motion thereto, the components may carry out their intended action, function, and/or procedure.

As discussed above, at least five systems of interchangeable shaft assembly (16) may be operatively coupled with at least five corresponding systems of handle (14). A first system comprises a frame system that couples and/or aligns the frame or spine of shaft assembly (16) with frame (28) of the handle (14). A second system is the latch system that releasably locks the shaft assembly (16) to the handle (14).

A third system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). Through closure drive system (30), anvil (50) pivots toward and away from staple cartridge (20) based on pivotal movement of closure trigger (32) toward and away from pistol grip (26).

A fourth system is an articulation and firing drive system operatively connecting firing trigger (33) of handle (14) with intermediate firing shaft (82) of the shaft assembly (16). As outlined above, the shaft attachment lug (80) operatively connects with the cradle (84) of the longitudinal drive member (86). This fourth system provides motorized actuation of either articulation joint (52) or staple cartridge (20), depending on the pivotal position of closure trigger (32). When closure trigger (32) is in a non-actuated pivotal position, the fourth system operatively connects articulation control rocker (112) with articulation joint (52), thereby providing motorized pivotal deflection of end effector (18) toward and away from the longitudinal axis of shaft assembly (11) at articulation joint (52). When closure trigger (32) is in an actuated pivotal position, the fourth system operatively connects firing trigger (33) with staple cartridge (20), resulting in stapling and cutting of tissue captured between anvil (50) and staple cartridge (20) in response to actuation of firing trigger (33).

A fifth system is an electrical system that can signal to control circuit (117) in handle (14) that the shaft assembly (16) has been operatively engaged with the handle (14), to conduct power and/or communicate signals between the shaft assembly (16) and the handle (14). In the present example, and as shown in FIG. 3, shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, now abandoned, the disclosure of which is incorporated by reference herein and/or U.S. Pub. No. 2015/0272575, issued as U.S. Pat. No. 9,913,642 on Mar. 13, 2018, the disclosure of which is incorporated by reference herein.

Other kinds of systems of interchangeable shaft assembly (16) that may be operatively coupled with at corresponding systems of the handle (14) will be apparent to those of ordinary skill in the art in view of the teachings herein.

As noted above, handle assembly (11) of the present example includes a graphical user interface (116). By way of example only, graphical user interface (116) may be used to display various information about the operational state of battery (110), the operational state of end effector (18), the operational state of articulation joint (52), the operational state of triggers (32, 33), and/or any other kinds of information. Other suitable kinds of information that may be displayed via graphical user interface will be apparent to those of ordinary skill in the art in view of the teachings herein.

Figure 6:
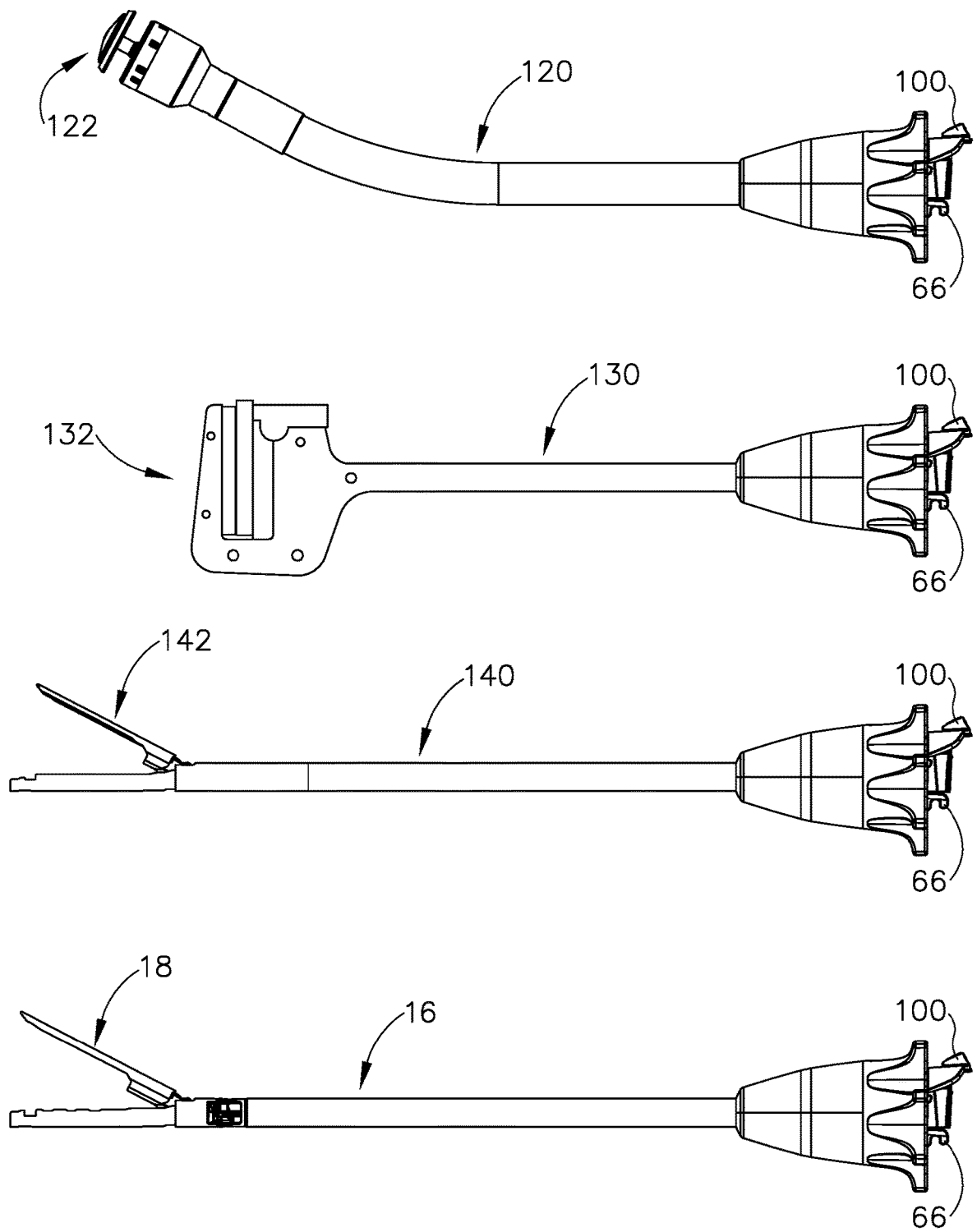
FIG. 6 depicts a side elevational view of an array of alternative shaft assemblies that may be used with the instrument of FIG. 1.

Handle assembly (11) may be configured for use in connection with interchangeable shaft assemblies that include end effectors that are adapted to support different sizes and types of staple cartridges, have different shaft lengths, sizes, and types, etc. By way of example only, FIG. 6 shows various different kinds of shaft assemblies (16, 120, 130, 140) that may be used with handle assembly (11). In particular, FIG. 6 shows a circular stapler shaft assembly (120) with an end effector (122) that is operable to perform a circular stapling operation (e.g., end-to-end anastomosis); a liner stapler shaft assembly (130) with an end effector (132) that is operable to perform a linear stapling operation; and a second endocutter shaft assembly (140) with an end effector (142) that is operable to perform the same kind of stapling and cutting operation as end effector (18). However, in this example, shaft assembly (140) is shorter than shaft assembly (16), shaft assembly (140) has a smaller diameter than shaft assembly (16), and end effector (142) is smaller than end effector (18). It should be understood that these various surgical stapling shaft assemblies (16, 120, 130, 140) are merely illustrative examples.

It should also be understood that control circuit (117) may be configured to detect the kind of shaft assembly (16, 120, 130, 140) coupled with handle assembly (11), and select a control algorithm suited for that particular kind of shaft assembly (16, 120, 130, 140). As another merely illustrative example, each shaft assembly (16, 120, 130, 140) may have a chip or other memory device storing the control algorithm suited for that particular kind of shaft assembly (16, 120, 130, 140); and control circuit (117) may receive and execute that control algorithm after shaft assembly (16, 120, 130, 140) is coupled with handle assembly (11).

In addition, handle assembly (11) may also be effectively employed with a variety of other interchangeable shaft assemblies including those assemblies that are configured to apply other motions and kinds of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

The various shaft assemblies (16) disclosed herein may employ sensors and various other components that require electrical communication with control circuit (117) in handled assembly (11). The electrical communications may be provided via mating electrical connectors (106, 108). By way of example only, such sensors and other components may be constructed and operable in accordance with at least some of the teachings of U.S. Pub. No. 2015/0272575, issued as U.S. Pat. No. 9,913,642 on Mar. 13, 2018, the disclosure of which is incorporated by reference herein. In addition, or in the alternative, instrument (10) may be constructed and operable in accordance with at least some of the teachings of any of the various other references that are cited herein.

It will be appreciated that the various teachings herein may also be effectively employed in connection with robotically-controlled surgical systems. Thus, the term "housing" or "body" may also encompass a housing, body, or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. By way of example only, the interchangeable shaft assemblies disclosed herein may be employed with any of the various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

II. End of Life Determination for Power Source

As noted above, instrument (10) of the present example includes battery pack (110) and control circuit (117). As shown in FIG. 5, battery pack (110) includes a power source (111) disposed therein. Power source (111) is configured to provide power to the various elements of instrument (10). However, power source (111) includes a finite amount of power and therefore degrades or loses power over time to eventually cease to provide sufficient power to operate instrument (10). The reduction in power or life below a disposal threshold and/or below that which is required to sufficiently power instrument (10) is referred to as the "end of life" of power source (111). While power source (111) is shown and described as disposed within battery pack (110), power source (111) may be coupled with instrument (10) in any other suitable fashion and may be disposed within any element of instrument (10) or separately associated with instrument (10) without being disposed in an element of instrument (10). Further, all or a portion of control circuit (117) may be disposed within battery pack (110).

Some versions of battery pack (110) and/or control circuit (117) may incorporate static end of life considerations for power source (111). In some versions of instrument (10), the end of life for power source (111) may be associated with a static number of uses. For example, after six firings of handle assembly (11), control circuit (117) may initiate the self-disposal mode of power source (111). However, this method may overestimate the actual electrical draw on power source (111) with respect to the firings and may lead to early initiation of the self-disposal mode while power source (111) remains viable.

Some versions of instrument (10) may incorporate dynamic considerations for determining a more accurate end of life power source (111). Life deduction and/or determination may be performed by control circuit (117) using variables or information generally from handle assembly (11), shaft assembly (16, 120, 130, 140), end effector (18, 122, 132, 142), battery pack (110), and/or power supply (111). More specifically, life deduction may be determined based on the rate of drain on power source (111), peaks of drain on power source (111), the amount of time power source (111) is active during a procedure, the number of sleep and wake cycles for power source (111), the number and intensity of firings for instrument (10), sensor operations such as a temperature sensor, the type of shaft assembly (16, 120, 130, 140) coupled to handle assembly (11), loads experienced by power source (111), the time elapsed from the manufacture of power source (111), the time elapsed from the first use of power source (111), and/or any other related metrics for dynamically calculating life deduction information.

A. Dynamic End of Life Determination for Power Source

Figure 7:
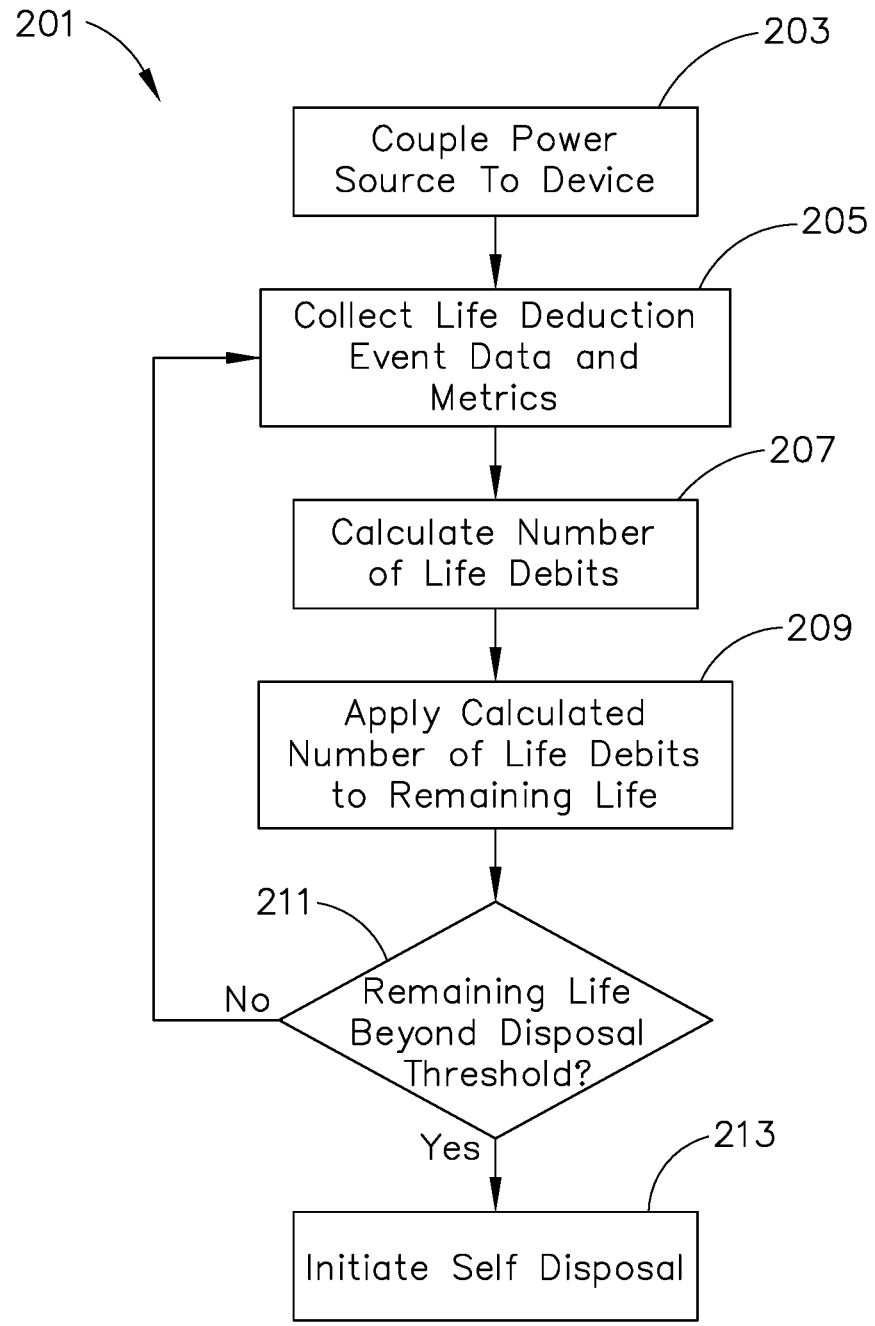
FIG. 7 depicts a flowchart of an exemplary method for determining the end of life for a power source of the instrument of FIG. 1.

FIG. 7 includes an example of a method (201) for use in dynamically determining an end of life for power source (111) and initiating the self-disposal mode. Method (201) begins with a step (203). In step (203), battery pack (110) is coupled to handle assembly (11) of instrument (10), which in turn couples power source (111) control circuit (117). Step (203) may be altered or omitted in those versions of instrument (10) where battery pack (110) and/or power source (111) is integrated within handle assembly (11).

In some versions of instrument (10), the coupling of battery pack (110) to handle assembly (11) initializes battery pack (110) and may also initiate timing features that track the total time battery pack (110) has been connected to instrument (10), which will be discussed in greater detail below. After battery pack (110) has been coupled to instrument (10), step (203) moves to a step (205). In step (205), life deduction event data and/or metrics are collected regarding the use of power source (111) as well as other elements of instrument (10). These events and metrics will be discussed in greater detail below, but may include information such as the type of shaft assembly (16, 120, 130, 140) attached to handle assembly (11) and the specific power requirements thereof, the number of non-use wake cycles of power source (111), and the environmental temperature when instrument (10) is fired. After life deduction event data and/or metrics are collected, method (201) moves to a step (207).

In step (207), control circuit (117) calculates a number of life debits corresponding to the power drained from power source (111) based on the life deduction event data and/or metrics. This calculation may be based on a single collected life deduction event data or metric. For example, the calculation may be based on the life deduction event which represents the largest amount of power use. The calculation may also be based on a combination of the collected events/metrics. Once the number of life debits are derived from the life deduction event data and/or metrics, method (201) proceeds to a step (209). In step (209), the calculated number of life debits are applied to the remaining life associated with power source (111). For example, power source (111) is currently viable for five lives and step (207) determines that the number of life debits is three. In this scenario, control circuit (117) applies the calculated number of life debits to the current lives and determines that power source (111) now has two lives remaining. In some versions of instrument (10), each life associated with power source (111) corresponds to a firing of handle assembly (11). In other versions of instrument (10), "life" is measured in the overall battery power remaining in power source (111) when power source (111) is embodied by a battery.

Once the remaining life of power source (111) is downwardly adjusted to account for the life deduction event data and metrics, method (201) proceeds to a step (211), step (211), a determination is made regarding whether the remaining life of power source (111) is beyond a set disposal threshold. In some versions of instrument (10), the disposal threshold relates to the amount of power required to conduct one or more firings of handle assembly (11). In some versions of instrument (10), the disposal threshold is a static amount of remaining battery life in power source (111). In other versions of instrument (10), a dynamic determination is made regarding the disposal threshold and the amount of power required to fire instrument (10) as currently configured. For example, the disposal threshold may take into account the specific shaft assembly (16, 120, 130, 140) connected to handle assembly (11) and the amount of power required to fire or actuate the connected shaft assembly (16, 120, 130, 140) and derive an appropriate disposal threshold from these features of instrument (10). If step (211) determines the remaining amount of life within power source (111) is not beyond the disposal threshold, step (211) returns to step (205), where additional life deduction event data and metrics are collected.

If step (211) determines the remaining amount of life within power source (111) is beyond the disposal threshold, method (201) proceeds to a step (213). In step (213), the self-disposal mode of power source (111) is initiated. The self-disposal mode may include an alert to the user that power source (111) is "dead" or otherwise unable to provide power to instrument (10). This alert may be provided through visual feedback such as through graphical user interface (116), audio feedback, or tactile feedback. The self-disposal mode may also include preventing the transmission of any power from power source (111) into instrument (10) or beyond control circuit (117) into handle assembly (11) or instrument (10). Initiating the self-disposal mode of power source (111) is directed to discouraging the use of instrument (10) in any further medical procedures, as the available power remaining in power source (111) may not be sufficient to complete the procedure.

In method (201) of the present example, the process of adjusting the life of power source (111) based on collected data is repeated until the life of power source (111) is below the set disposal threshold. Once the disposal threshold is reached, instrument (10) is ready for disposal or other preventative measures to ensure instrument (10) is not further used in a medical procedure.

B. Life Deduction Event Data and Metrics

Figure 8:
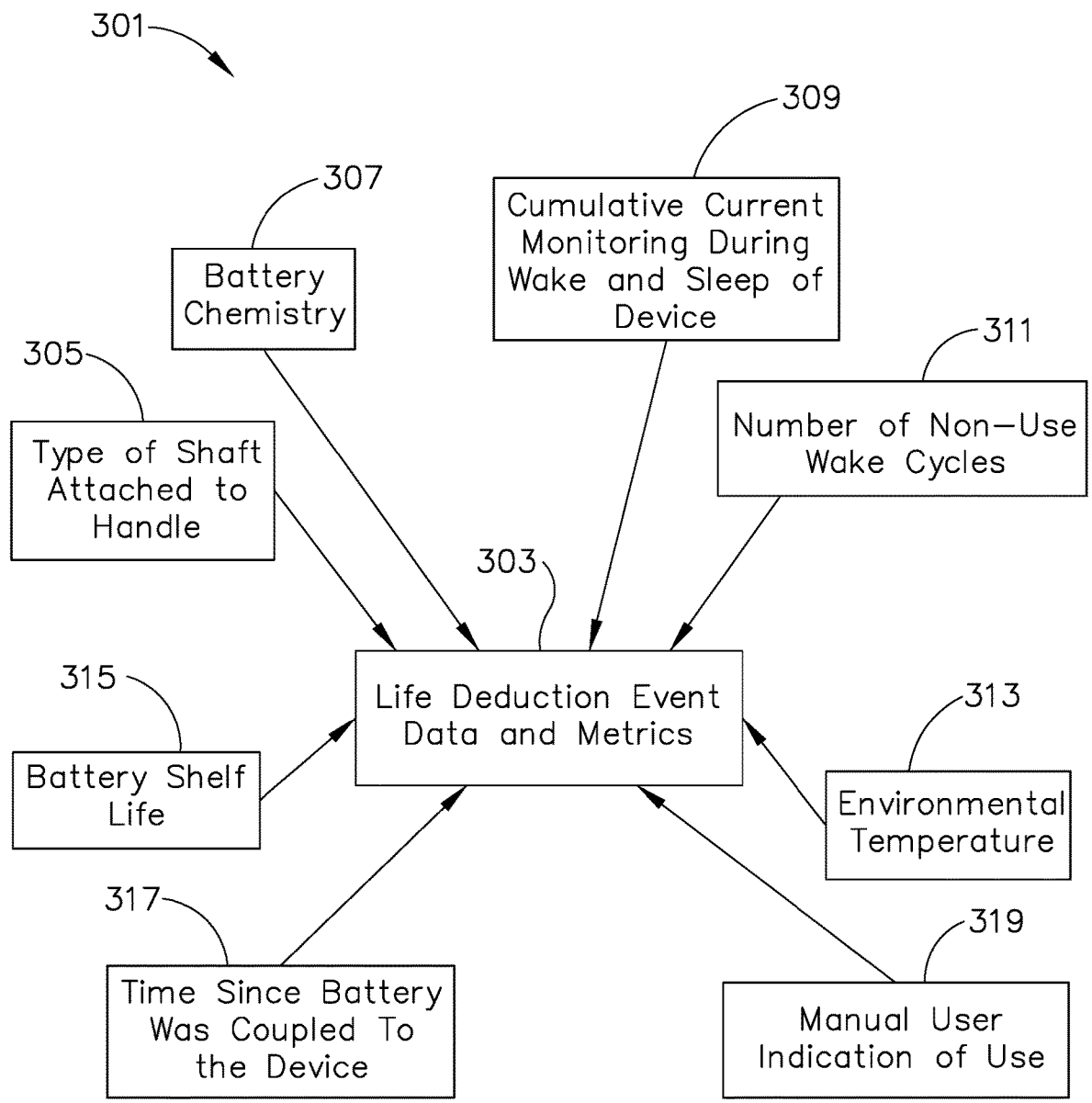
FIG. 8 depicts a schematic view of exemplary life deduction event data and metrics for use in determining the end of life for the power source of the instrument of FIG. 1.

As shown in FIG. 7, method (201) uses collected life deduction event data and metrics to dynamically determine an end of life for power source (111). An exemplary method (301) for collecting life deduction event data and metrics is depicted schematically in FIG. 8. FIG. 8 depicts the various methods or types of data available for collection in various versions of instrument (10). Each data collection mechanism of method (301) is shown as providing data into a block (303). Block (303) represents the storage of the life deduction event data and metrics for use by instrument (10). In some versions, the storage of the life deduction event data and metrics may be facilitated by control circuit (117) by way of a memory or register or any other mechanism for storing data. In other versions of instrument (10), block (303) is omitted and the life data collected by instrument (10) is used in real-time by control circuit (117) to determine the changes in the overall life of power source (111). Method (201) may use any one or more of the following examples of life deduction event data and metrics for use determining the end of life for power source (111).

1. Type of Shaft Attached to Handle

A block (305) represents the collection of data relating to the specific shaft assembly (16, 120, 130, 140) connected to handle assembly (11). Inasmuch as each shaft assembly (16, 120, 130, 140) may require a different amount of power from power source (111), block (305) collects information regarding which shaft assembly (16, 120, 130, 140) is attached to handle assembly (11) and how much power is used in each firing. For example, if power source (111) begins with ten lives, firing instrument (10) with shaft assembly (16) attached thereto may debit two lives, while firing instrument

(10) with shaft assembly (120) attached thereto may debit four lives. The differences in life debits between shaft assemblies (16, 120, 130, 140) may be based on the different work being done by the particular shaft assembly (16, 120, 130, 140), the different stress on motor (118), or the different size or style of end effector (18, 122, 132, 142) disposed at the distal end of the particular shaft assembly (16, 120, 130, 140). For example, a right-angled shaft assembly similar to shaft assembly (130) may require a different amount of power from power source (111) compared to a curved shaft assembly similar to shaft assembly (120). In another example, end effector (18, 122, 132, 142) may require a different amount of power from power source (111) compared to end effector (142).

Figure 9:
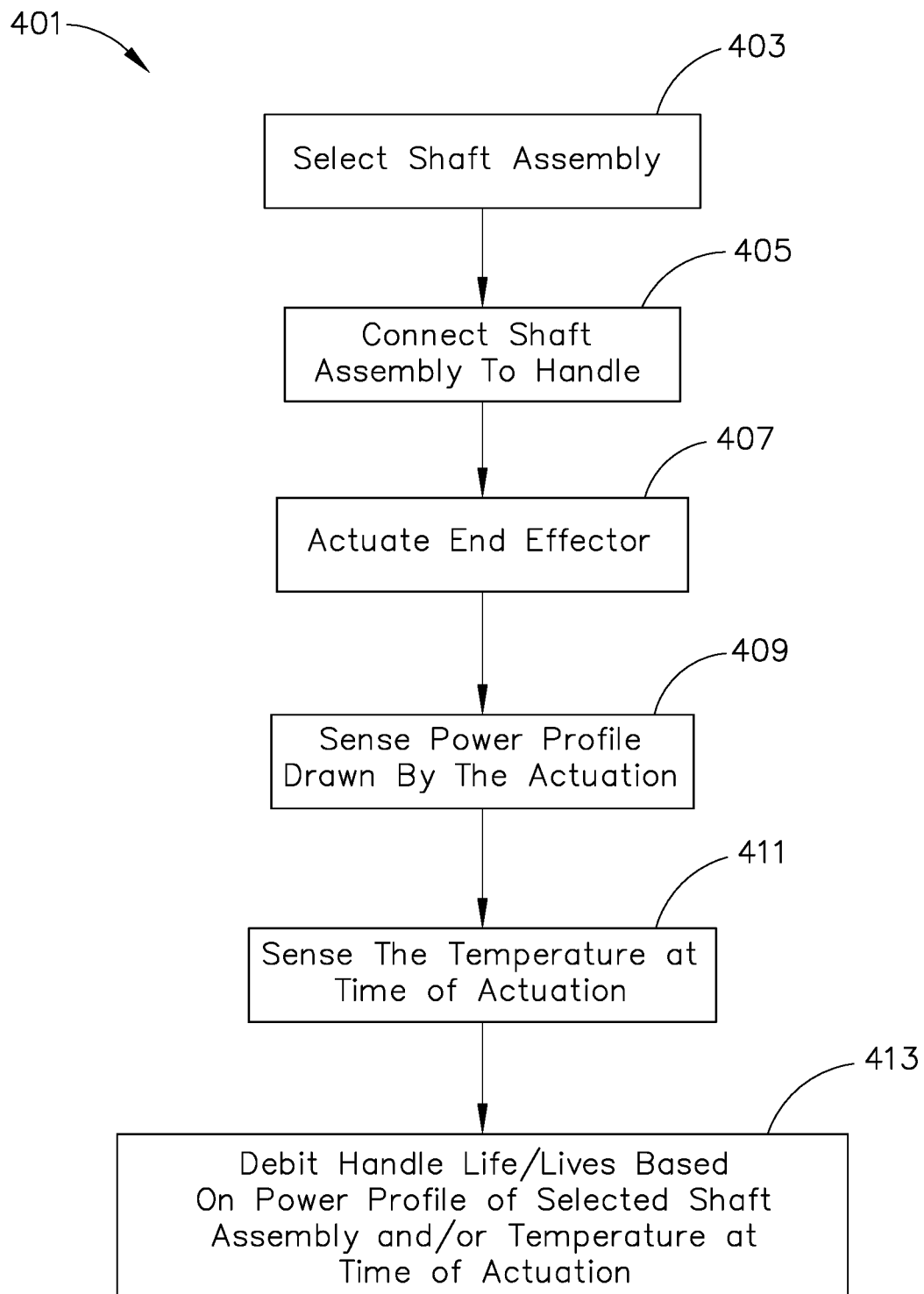
FIG. 9 depicts a flowchart of an exemplary method for determining the number of life debits to apply to the handle assembly of the instrument of FIG. 1.

As shown in FIG. 9, a method (401) may be used in some versions of instrument (10) to determine the amount of life debits for a firing/use of handle assembly (11). Method (401) begins with a step (403), whereby a shaft assembly (16, 120, 130, 140) is selected by a user. By way of example only, the user may interact with graphical user interface (116) to select the particular shaft assembly (16, 120, 130, 140) at hand from a listing of shaft assemblies (16, 120, 130, 140) that are compatible with handle assembly (11). In some other versions, shaft assembly (16, 120, 130, 140) includes a chip or other feature that communicates with a complementary reader or other feature of handle assembly (11), such that control circuit (117) may automatically identify the particular kind of shaft assembly (16, 120, 130, 140) based on the interaction between these complementary features of handle assembly (11) and shaft assembly (16, 120, 130, 140) after shaft assembly (16, 120, 130, 140) is coupled with handle assembly (11). As another merely illustrative example, control circuit (117) may execute an initialization routine through shaft assembly (16, 120, 130, 140) (e.g., momentarily actuating a movable component of shaft assembly (16, 120, 130, 140), etc.) to identify the particular kind of shaft assembly (16, 120, 130, 140) coupled with handle assembly (11). Other suitable ways in which control circuit (117) may determine the kind of shaft assembly (16, 120, 130, 140) coupled with handle assembly (11) will be apparent to those of ordinary skill in the art in view of the teachings herein.

After the type of shaft assembly (16, 120, 130, 140) is selected or otherwise determined, method (401) thereafter moves to a step (405), whereby the selected shaft assembly (16, 120, 130, 140) is connected to handle assembly (11). Thereafter, method (401) moves to a step (407), whereby the user actuates end effector (18, 122, 132, 142) of the selected shaft assembly (16, 120, 130, 140). Thereafter, method (401) moves to a step (409).

In step (409), power source (111) or control circuit (117) senses the power drain on power source (111) via the actuation of end effector (18, 122, 132, 142). The amount power drawn through the actuation of the particular end effector (18, 122, 132, 142) may be directly used to determine the life debits for the firing. For example, a firing may draw three units of power from power source (111). The three unit amount may then be used to directly determine life debits. In other versions of method (401), the amount of power drawn through actuation of the particular end effector (18, 122, 132, 142) may be used indirectly to determine the life debits for firing. In the example above, the power draw of three units may be used by control circuit (117) to derive or select a power profile based on the power draw. This information may be provided in a lookup table in a memory associated with control circuit (117) or may be available through another mechanism. The selected power profile may then provide the number of life debits to control circuit (117).

Power profiles may be used to simplify the calculation of life debits by linking a power profile to a range of power drawn through a firing. For example, power drawn in the range of three to seven units via a firing may correspond to a first power profile. The first power profile may then be associated with two life debits per firing. Power profiles may also be helpful in preserving power drawn from power source (111) by eliminating the need to continuously sense the amount of power drawn from a firing. In some versions, once the first firing is completed and the power profile is determined, subsequent sensing of power drawn from a firing is omitted. Control circuit (117) may apply the same number of life debits for each subsequent firing based on the power profile determined from the initial firing.

After sensing the power drawn through an actuation of end effector (18, 122, 132, 142), method (401) moves to a step (411). In step (411), the temperature at the time of the firing/actuation of end effector (18, 122, 132, 142) is sensed and considered. As will be discussed in greater detail below, the temperature at the time of firing may affect the life debit amount. However, step (411) is an optional step that may be omitted in some version of method (401).

After sensing the temperature at the time of actuation, step (411) proceeds to a step (413), whereby the number of lives used by the firing are calculated based on the power drawn and the temperature at the time of firing. Thereafter, the lives are debited from the remaining number of lives.

2. Battery Chemistry

In those versions of power source (111) where power source (111) is embodied in a battery, a block (307) represents the collection of data relating to the charge of the battery of power source (111). In particular, some versions of block (307) may consider the depletion of the voltage of power source (111) over time. In some versions, block (307) may continuously pass voltage information to block (303) to consider the impact of the voltage over time for power source (111). In other versions, block (307) monitors the voltage of power source (111) over time to determine whether the voltage has decayed below a particular threshold value. Upon passing the threshold, block (307) notifies block (303) for further consideration and for use of this information as life deduction event data.

In some versions, the preferred threshold of depletion is 2.5 volts for a particular battery of power source (111). For example, power source (111) may comprise a "CR123" single cell battery based on $Li/SO_2$ chemistry. In other versions, power source (111) may include a pack of "CR123" batteries, with a 10 volt threshold of depletion. In other versions of power source (111) a threshold of depletion may be provided in a range (e.g., a range of 1.5-2.6 volts for a threshold of depletion). In other versions of power source (111), a battery based on $Li/MnO_2$ chemistry may have a wider threshold of depletion range because batteries based on $Li/MnO_2$ chemistry may be associated with a more sloped voltage decay as the cell depletes.

3. Cumulative Current Monitoring During Wake and Sleep of Device

A block (309) collects data relating to a current drawn from power source (111) and provides this life deduction event data and metrics to block (303) for use in determining the end of life for power source (111). In some versions of block (309), the current of power source (111) is cumulatively collected to derive a continuously updating total current drawn from power source (111). In those versions of instrument (10) where power source (111) is embodied in a battery, the cumulative current drawn from power source (111) may be used to derive the remaining life of the battery and estimate the remaining life of power source (111).

In some versions of block (309), data regarding the current drawn from power source (111) is collected while instrument (10) is in use. For example, an internal accelerometer (not shown) may indicate to control circuit (117) that instrument (10) is being handled and in use, which initiates the collection of data relating to the current drawn from power source (111) during this period of use. This data is passed to block (303) for use in the end of life calculations with respect to power source (111).

In addition to collecting the current drawn from power source (111) during use, the way in which instrument (10) is used may also be incorporated into the collection of data in block (309). For example, an application of instrument (10) involving a heavy current draw or heavy current draws from power source (111) in quick succession to each other could be used to modify the estimation of remaining power for power source (111). In this scenario, block (309) may collect the instantaneous measure of voltage at a predefined resistance level during the use of instrument (10) to capture additional current draw data. In those versions of power source (111) where power source (111) is embodied in a battery, overusing the battery chemistry may result in a larger amount of remaining life being drawn from power source (111) when compared to a steady current drawn from the battery over time. Thus, some versions of block (309) are configured to consider significantly higher current draw or erratic current draw rate in the monitoring of current use and associated data and incorporate these considerations into the estimation of life for power source (111).

In other versions of block (309), data regarding the current drawn from power source (111) is collected while instrument (10) is not in use. For example, an internal accelerometer (not shown) may indicate to control circuit (117) that instrument (10) is not in use after instrument (10) remains stationary for a predetermined duration of time. Similarly, a user may actuate a button or power-down sequence on instrument (10) to transition instrument (10) into a sleep mode. In response to instrument (10) being in a sleep mode or otherwise not in use, data collection regarding the current drawn from power source (111) during this period of non-use is collected. In some versions of block (309), the amount of current drawn during non-use of instrument (10) may be compared and considered along with a predefined threshold for acceptable non-use current draw. In those versions of instrument (10) where power source (111) is embodied in a battery, this predefined threshold may relate to an acceptable power leakage level over an expected or predefined amount of time. In those versions, if the period of non-use for instrument (10) is over a longer than expected amount of time, this information may also be used to affect the end of life calculations for power source (111).

In other versions of block (309), data regarding the current drawn from power source (111) is collected while instrument (10) is in use and while instrument (10) is in sleep mode or otherwise not in use. In these versions, all the collected current draw information or use metrics from power source (111) is incorporated into life deduction event data and metrics and provided to block (303) for consideration with respect to the end of life for power source (111).

4. Number of Non-Use Wake Cycles

A block (311) represents the collection of data relating to the number of non-use wake cycles for power source (111) As discussed above, power source (111) may transition between a sleep mode or period of non-use to a period of use or a wake mode, whereby the user may manipulate instrument (10) and actuate a firing or other power draining operation of handle assembly (11). In some versions, instrument (10) may include an accelerometer (not shown) or other motion sensing element that triggers a transition out of the sleep mode and into the wake mode when a user picks up or otherwise moves instrument (10). In other versions, instrument (10) may include a power-on button or a graphical area on graphical user interface (116) that is used to transition instrument (10) out of sleep mode and into the wake mode.

However, while instrument (10) is in the wake mode, the user may decide not to fire or otherwise actuate handle assembly (11) to draw a large amount of power from power source (111). For example, if instrument (10) is manually moved from one storage area to another, some versions of instrument (10) will enter the wake mode upon movement. However, in this scenario, instrument (10) does not initiate a firing or large power draw from power source (111) before instrument (10) again enters the sleep mode. Block (311) collects the number of non-use wake cycles and provides this life deduction event data to block (303) for use in determining the end of life for power source (111).

5. Environmental Temperature

A block (313) represents the collection of data relating to the environmental temperature associated with power source (111). In some versions of block (313), the environmental temperature at the time of use or the time of firing handle assembly (11) is relevant to the overall life of power source (111). For example, in those versions of instrument (10) where power source (111) is embodied in a battery, the environmental temperature at the time of firing handle assembly (11) can significantly affect the remaining life of the battery due to the chemical interactions within battery. In some versions of power source (111), the drain on a battery in a 90° F. room may be associated with a 10% difference when compared to a 70° F. room.

As shown in FIG. 5, a temperature sensor (314) may be incorporated into instrument (10), and specifically into handle assembly (11) to facilitate the determination of the environmental temperature at the time of use for instrument (10). Temperature sensor (314) is positioned to sense the temperature of the environment in which instrument (10) is being used, without being heated by the operator's hand, motor (118), or other features of instrument (10) that may tend to heat up during normal use of instrument (10). As represented by block (313), temperature sensor (314) collects environmental temperature data and provides this data to control circuit (117) for use in determining the end of life for power source (111). Control circuit (117) uses the environmental temperature measurements from temperature sensor (314) to determine the per use or per firing cost or effect of the measured temperature on power source (111) and update the end of life considerations accordingly. As shown in FIG. 8, block (313) collects the environmental temperature data and provides this life deduction event data to block (303) for use in determining the end of life for power source (111).

The environmental data may be incorporated into a larger method for determining the number of life debits for power source (111). As shown in FIG. 9, some collection methods for life deduction event data may incorporate the environmental temperature measurement into a larger method, such as method (401). As depicted in block (411), the environmental temperature at the time of actuation of end effector (18, 122, 132, 142) may affect the calculation of life debits and power drain considerations.

6. Battery Shelf Life

As shown in FIG. 8, a block (315) collects shelf life data and provides this life deduction event data to block (303) for use in determining the end of life for power source (111). In those versions of power source (111) where power source (111) is embodied in a battery, block (315) represents the collection of data relating to the shelf life of the battery within instrument (10). In some versions of block (315), the battery is associated with a time duration for determining expiration, referred to hereinafter as a shelf life. In some versions of instrument (10), a real-time clock (not shown) may be provided in instrument (10) for determining the amount of time remaining in the shelf life of power source (111). In other versions, control circuit (117) tracks the time remaining in the shelf life of power source (111). Upon reaching the end of the shelf life for power source (111), instrument (10) transitions into the disposal mode.

In some versions of instrument (10), the measure of the relative life remaining for instrument (10) with respect to the shelf life is a separate consideration from the other life deduction event data and metrics. In these versions, regardless of the other collected data and metrics, if the battery of power source (111) has reached the end of its shelf life, instrument (10) transitions into the disposal mode.

Figure 10:
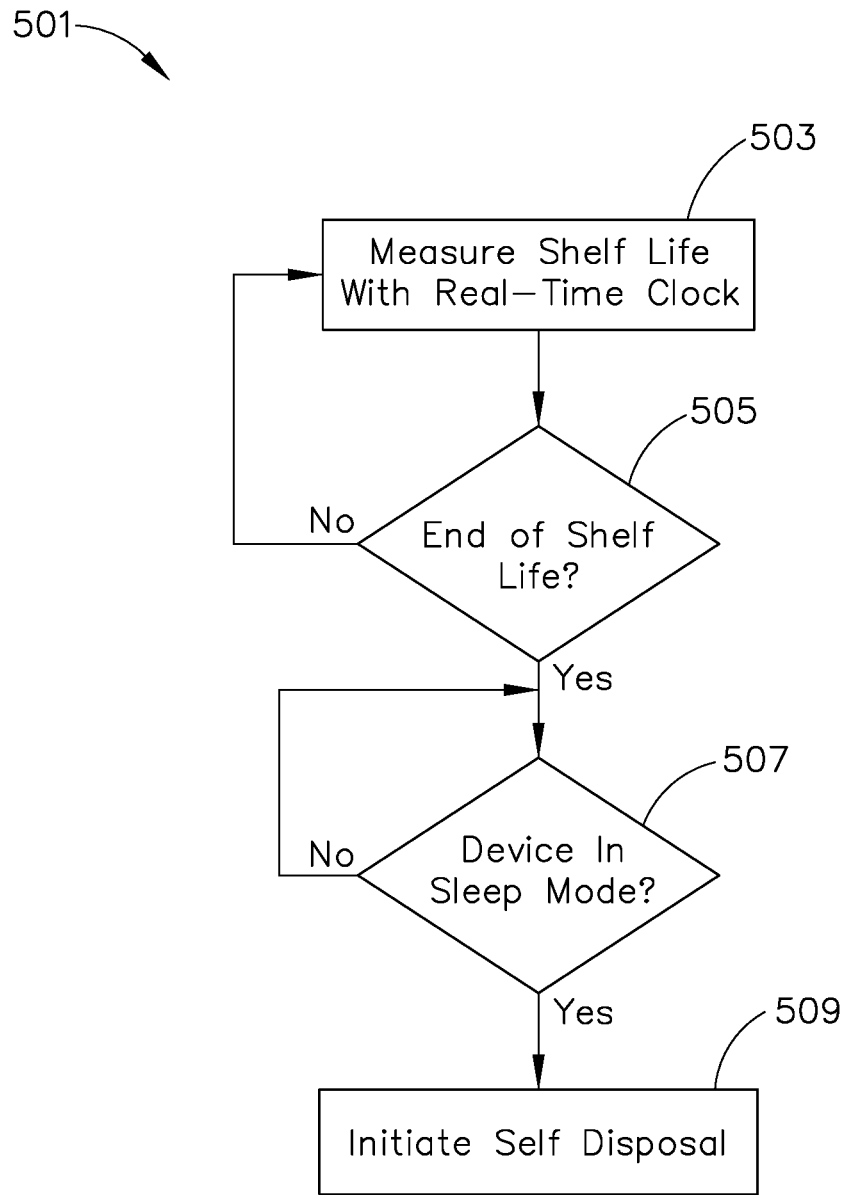
FIG. 10 depicts a flowchart of an exemplary method for initiating self-disposal mode of the power source of the instrument of FIG. 1.

Inasmuch as moving instrument (10) into the disposal mode during a medical procedure may be disruptive to the medical procedure, a method (501) is provided for preventing instrument (10) from moving to the disposal mode during a medical procedure. As shown in FIG. 10, method (501) begins with a step (503), whereby a real-time clock associated with instrument (10) measures and tracks the shelf life of power source (111). Thereafter, step (503) moves to a step (505), whereby control circuit (117) or another element of instrument (10) determines whether power source (111) has reached the end of its shelf life. If step (505) determines power source (111) has not reached the end of its shelf life, step (505) proceeds back to step (503) to continuously monitor the remaining shelf life of power source (111). If step (505) determines power source (111) has reached the end of its shelf life, step (505) proceeds to a step (507).

In step (507), control circuit (117) or another element of instrument (10) determines if instrument (10) is in the sleep mode, indicating instrument (10) is currently not being used in a medical procedure. If step (507) determines that instrument (10) is not in the sleep mode, step (507) loops back on itself to continuously determine the status of instrument (10). The continuous looping of step (507) while instrument (10) is not in the sleep mode ensures instrument (10) will not move to the disposal mode while instrument (10) is being used. If step (507) determines instrument (10) is in the sleep mode, step (507) proceeds to a step (509). In step (509), instrument (10) and/or control circuit (117) initiates the disposal mode and the user is no longer able to actuate features of instrument (10).

7. Time Since Battery was Coupled to the Device

In those versions of power source (111) where power source (111) is embodied in a battery, a block (317) represents the collection of data relating to the time since the battery was coupled to instrument (10). This timing data is related to the overall shelf life of power source (111). However, while the shelf life of power source (111) may be a set amount of time, the duration of this time may be affected by coupling power source (111) with instrument (10) as the slow drain on power source (111) from instrument (10) may ultimately reduce the shelf life. For example, if a battery has a shelf life of one year in an uncoupled state, the same battery may have a shelf life of six months after being coupled with instrument (10), whereby a small parasitic power draw on power source (111) is introduced or increased. Block (317) collects information regarding the time that has elapsed since power source (111) was coupled with instrument (10) and provides this life deduction event data to block (303) for use in determining the end of life for power source (111).

8. Manual User Indication of Use

Figure 11:
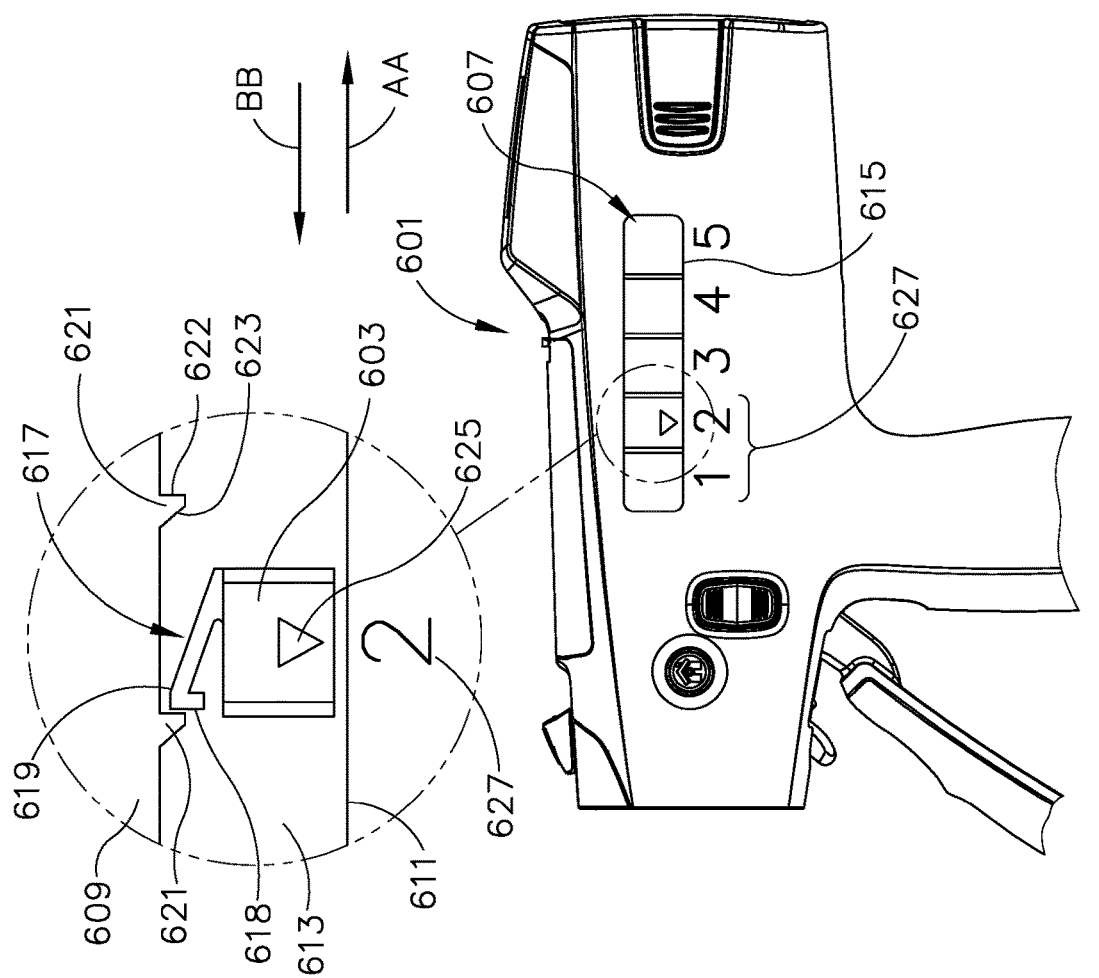
FIG. 11 depicts a side elevational view of a variation of the handle assembly of the instrument of FIG. 1, with an exemplary manual input clip.
Figure 12:
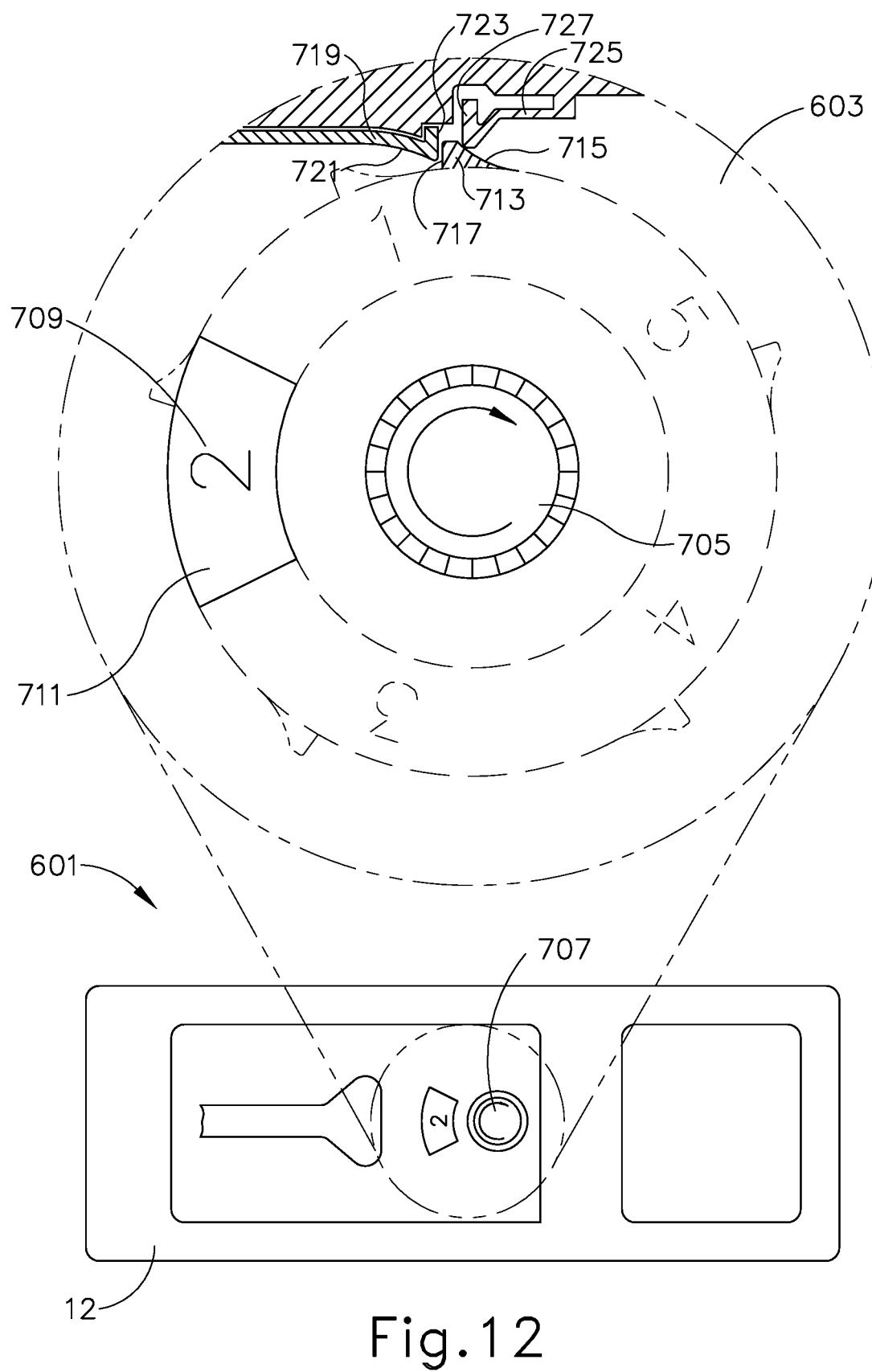
FIG. 12 depicts a top plan view of another variation of the handle assembly of the instrument of FIG. 1, with an exemplary manual input dial.

As shown in FIGS. 8, 11, and 12, a block (319) receives manually entered use data from the user and provides this life deduction event data to block (303) for use in determining the end of life for power source (111). With respect to firings or actuations of instrument (10), each time a user fires or actuates handle assembly (11), the user may voluntarily and manually index the use to instrument (10). By providing the use information manually, control circuit (117) may either directly rely on the provided use information or control circuit (117) may use the provided use information to verify or cross-check the internal use calculations facilitated by control circuit (117).

The user may provide this information through graphical user interface (116) by actuating a graphical button or buttons disposed thereon. The graphical button may be in the form of a "+" sign, a "−" sign, an arrow graphic, or any other graphical mechanism for providing a way for the user to increase or decrease the indicated number of firings or uses of handle assembly (11).

As shown in FIGS. 11 and 12, the user may also provide this information manually through a manual input clip (601) or a manual input dial (701) incorporated with instrument (10). As shown in FIG. 11, manual input clip (601) includes a slider (603) that is slidably disposed within a track (607). Track (607) is defined by a first rail (609), a second rail (611), and a back wall (613) extending therebetween. Disposed between first rail (609), second rail (611), and back wall (613), slider (603) is held therein by housing (12) of handle assembly (11). In this orientation, slider (603) is disposed between back wall (613) and housing (12) in a first axis, between first rail (609) and second rail (611) in a second axis, and free to slide in a third axis. To project the placement of slider (603) to the user, housing (12) defines a window (615) where a portion of slider (603) is visible therethrough.

Slider (603) includes a cam clip (617) that is biased toward first rail (609). Cam clip (617) includes a locking surface (618) and a cam surface (619) oriented to face first rail (609). A series of spaced apart detents (621) are disposed on first rail (609), with each detent (621) having a locking surface (622) and a cam surface (623) disposed thereupon and oriented to face slider (603). As slider (603) is moved along in a first direction, indicated by Arrow AA, cam surface (619) of cam clip (617) presses against cam surface (623) of the closest detent (621) to overcome the bias of cam clip (617) and allow slider (603) to move in the direction of Arrow AA. Once cam clip (617) passes the closet detent (621), cam clip (617) springs back to its natural orientation. Slider (603) is prevented from moving in the direction of Arrow BB past the particular detent (621) by locking surface (618) of cam clip (617) abutting locking surface (622) of detent (621). In this way, manual input dip (601) includes a one-way ratchet to allow indexing of use/firings in only one direction.

Slider (603) may include a bump or outcropping (not shown) for the user to manually manipulate to move slider (603) in the direction of Arrow AA after a firing. To depict the number of firings to the user, slider (603) may also include an indicia (625) such as an arrow pointing down. A corresponding indicia (627) disposed on housing (12) around window (615) allows the user to "point" to a particular number/indicia to manually indicate to instrument (10) how many firings or uses of instrument (10) have occurred. As shown in FIG. 11, the arrow shaped indicia (625) points to a number "2" indicia (627) to depict that instrument (10) has been fired two times.

In some versions of manual input clip (601), slider (603) may be coupled with control circuit (117) to provide feedback into instrument (10) regarding the number of firings the user believes have occurred. In these versions of manual input clip (601), slider (603) may be coupled with a particular resistance internal to instrument (10), which may then be used by control circuit (117) to indicate the number of uses or firings performed by the user. These versions may also be used to display any discrepancies between the user indexed number of firings/uses and the number of firings/ uses calculated by control circuit (117). Various suitable features that may be used to provide communication of use indications from slider (603) to control circuit (117) will be apparent to those of ordinary skill in the art in view of the teachings herein.

A user may readily observe the location of slider (603) and the associated indicia (625, 627) to view the uses/firings count without powering on instrument (10) and draining power from power source (111). In other circumstances where power source (111) is not coupled with instrument (10), the user may still observe the indicated number of firings/uses. Further, the visible indication of firings/uses may be useful in a sterilization area to reduce the risk that a device with no remaining firings/uses is put through the sterilization process. This may also prevent an unusable instrument (10) from being shipped or transported to an operating room.

Alternatively, rather than using manual input clip (601) for indicating firings/uses, personnel in the sterilization area may use manual input clip (601) to indicate the number of times instrument (10) has been sterilized. This feedback may be desired rather than an indication of firings/uses in certain environments or circumstances.

As shown in FIG. 12, manual input dial (701) generally includes many of the features of manual input clip (601). Manual input dial (701) includes a dial (703) with a control knob (705) extending therefrom. Dial (703) is pressed between an internal portion of handle assembly (11) and housing (12), with control knob (705) extending through an opening (707) in housing (12). A series of numbers or other indicia (709) is disposed on dial (703) and used to visually indicate the number of uses/firings. A window (711) is defined by housing (12) and sized to depict indicia (709) therethrough. As dial (703) is turned, different numbers of indicia (709) are displayed to the user through window (711) to indicate either the number of uses/firings of instrument (10) used by the user, or the number of uses/firings remaining in instrument (10).

A series of spaced apart detents (713) are disposed on dial (703), with each detent (713) having a cam surface (715) and a locking surface (717). A cam clip (719) is provided inside housing (12), with cam clip (719) having a cam surface (721) and a locking surface (723). Cam clip (719) is biased toward dial (703). As the user manipulates control knob (705) to turn dial (703), detents (713) rotate within housing (12). As dial (703) moves, cam surface (715) of detent (713) presses against cam surface (721) of cam clip (719), pressing on cam clip (719) sufficiently to overcome the bias and allow detent (713) to pass thereover. Once detent (713) passes cam clip (719), locking surface (723) of cam clip (719) abuts locking surface (717) of detent (713) to prevent dial from moving in the opposite direction. In some versions of manual input dial (701), another cam clip may provide a mechanism for locking detent (713) into place after detent (713) passes over cam clip (719). As shown in FIG. 12, a cam clip (725) may be provided, biased toward control knob (705). Cam clip (725) includes a locking surface (727) for abutting cam surface (715) of detent (713) and holding detent (713) between cam clip (719) and cam clip (725) after detent (713) passes over cam clip (719).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a handle assembly; (b) a power source coupled with the handle assembly; and (c) a control circuit coupled with the handle assembly and the power source, wherein the handle assembly, the power source, and the control circuit are configured to drive an end effector of a shaft assembly coupled with the handle assembly to perform an operation on tissue, wherein the control circuit is configured to receive life deduction event data, wherein the control circuit is configured to determine an end of life for the power source based on the life deduction event data.

Example 2

The instrument of Example 1, wherein the control circuit is configured to initiate a self-disposal mode of the power source when the power source reaches the determined end of life.

Example 3

The instrument of any one or more of Examples 1 through 2, wherein the control circuit is configured to transition the instrument between a wake mode and a sleep mode, wherein the control circuit is configured to initiate a self-disposal mode of the power source when the power source reaches the determined end of life and the power source is in the sleep mode.

Example 4

The instrument of any one or more of Examples 1 through 3, wherein the life deduction event data includes a type of a shaft assembly coupled with the handle assembly.

Example 5

The instrument of any one or more of Examples 1 through 4, wherein the life deduction event data includes a power profile of a shaft assembly coupled with the handle assembly.

Example 6

The instrument of Example 5, wherein the control circuit is configured to determine the power profile based at least in part on a first actuation of a user input of the handle assembly.

Example 7

The instrument of any one or more of Examples 1 through 6, wherein power source includes a battery having a voltage, wherein the control circuit is configured to monitor the voltage, wherein the life deduction event data includes the voltage of the battery.

Example 8

The instrument of any one or more of Examples 1 through 7, wherein the control circuit is configured to monitor a current of the power source while the power source is in a wake mode, wherein the life deduction event data includes the current of the power source.

Example 9

The instrument of any one or more of Examples 1 through 8, wherein the control circuit is configured to monitor a current of the power source while the power source is in a sleep mode, wherein the life deduction event data includes the current of the power source.

Example 10

The instrument of any one or more of Examples 1 through 9, wherein the control circuit is configured to determine a number of non-use wake cycles associated with the power source, wherein the life deduction event data includes the number of non-use wake cycles.

Example 11

The instrument of any one or more of Examples 1 through 10, further comprising a temperature sensor associated with the handle assembly, wherein the life deduction event data includes a temperature provided by the temperature sensor.

Example 12

The instrument of any one or more of Examples 1 through 11, wherein the life deduction event data includes a shelf life associated with the power source.

Example 13

The instrument of any one or more of Examples 1 through 12, wherein the control circuit is configured to determine an amount of time since the power source was coupled to the handle assembly, wherein the life deduction event data includes the amount of time.

Example 14

The instrument of any one or more of Examples 1 through 13, further comprising a manual input clip, wherein the manual input clip is configured to generate a signal, wherein the life deduction event data includes the signal generated by the manual input clip.

Example 15

The instrument of any one or more of Examples 1 through 14, further comprising a manual input dial, wherein the manual input dial is configured to generate a signal, wherein the life deduction event data includes the signal generated by the manual input dial.

Example 16

A method of determining an end of life for a power source of a surgical instrument, the method comprising: (a) coupling a power source with a handle assembly of a surgical instrument; (b) monitoring a life deduction event; (c) collecting a life deduction event data from the life deduction event; and (d) calculating an end of life for the power source based at least in part on the life deduction event data.

Example 17

The method of Example 16, further comprising: (a) coupling a shaft assembly to the handle assembly; (b) firing the handle assembly to actuate the shaft assembly; and (c) collecting a power drain on the power source associated with the firing of the handle assembly, wherein the life deduction event data includes the power drain on the power source associated with the firing of the handle assembly.

Example 18

The method of any one or more of Examples 16, through 17, further comprising: (a) determining whether a shelf life of the power source has expired; (b) determining whether the instrument is in a sleep mode; and (c) initiating a self-disposal mode of the power source when the shelf life has expired and the instrument is in the sleep mode.

Example 19

The method of any one or more of Examples 1 through 18, further comprising: (a) transforming the life deduction event data into a life debit amount; (b) debiting the life debit amount from a life associated with power source; (c) determining whether the life is beyond a disposal threshold; and (d) in response to determining the life is beyond the disposal threshold, initiating a self-disposal mode of the power source.

Example 20

A method of initiating a self-disposal mode of a power source of a surgical instrument, the method comprising: (a) receiving a life deduction event data; (b) in response to receiving the life deduction event data, calculating a life debit amount based on the life deduction event data; (c)

debiting the life debit amount from a life associated with the power source; (d) determining whether the life is beyond a disposal threshold; and (e) in response to determining the life is beyond the disposal threshold, initiating a self-disposal mode of the power source.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 15/634,418, entitled "Surgical Instrument with Integrated and Independently Powered. Displays," filed Jun. 27, 2017, issued as U.S. Pat. No. 10,163,309 on Dec. 25, 2018, the disclosure of which is incorporated by reference herein. Various suitable ways in which the teachings herein may be combined with the teachings of U.S. patent application Ser. No. 15/634,418, issued as U.S. Pat. No. 10,163, 309 on Dec. 25, 2018, will be apparent to those of ordinary skill in the art in view of the teachings herein.

In addition to the foregoing, the teachings herein may be readily combined with the teachings of U.S. patent application Ser. No. 15/634,436, entitled "Battery Pack with Integrated Circuit Providing Sleep Mode to Battery Pack and Associated Surgical Instrument," filed on Jun. 27, 2017, issued as U.S. Pat. No. 10,639,018 on May 5, 2020, the disclosure of which is incorporated by reference herein. Various suitable ways in which the teachings herein may be combined with the teachings of U.S. patent application Ser. No. 15/634,436 , issued as U.S. Pat. No. 10,639,018 on May 5, 2020, will be apparent to those of ordinary skill in the art in view of the teachings herein.

In addition to the foregoing, the teachings herein may be readily combined with the teachings of U.S. patent application Ser. No. 15/634,452, entitled "Battery Powered Surgical Instrument with Dual Power Utilization Circuits for Dual Modes," filed on Jun. 27, 2017, issued as U.S. Pat. No. 10,511,065 on Dec. 17, 2019, the disclosure of which is incorporated by reference herein. Various suitable ways in which the teachings herein may be combined with the teachings of U.S. patent application Ser. No. 15/634,452, issued as U.S. Pat. No. 10,511,065 on Dec. 17, 2019, will be apparent to those of ordinary skill in the art in view of the teachings herein.

In addition to the foregoing, the teachings herein may be readily combined with the teachings of U.S. patent application Ser. No. 15/634,475, entitled "Powered Surgical Instrument with Latching Feature Preventing Removal of Battery Pack," filed on Jun. 27, 2017, published as U.S. Pub. No. 2018/0368848 on Dec. 27, 2018, the disclosure of which is incorporated by reference herein. Various suitable ways in which the teachings herein may be combined with the teachings of U.S. patent application Ser. No. 15/634,475, published as U.S. Pub. No. 2018/0368848 on Dec. 27, 2018, will be apparent to those of ordinary skill in the art in view of the teachings herein.

In addition to the foregoing, the teachings herein may be readily combined with the teachings of U.S. patent application Ser. No. 15/634,497, entitled "Modular Powered Electrical Connection for Surgical Instrument with Features to Prevent Electrical Discharge" filed on Jun. 27, 2017, issued as U.S. Pat. No. 10,667,812 on Jun. 2, 2020, the disclosure of which is incorporated by reference herein. Various suitable ways in which the teachings herein may be combined with the teachings of U.S. patent application Ser. No. 15/634,497, issued as U.S. Pat. No. 10,667,812 on Jun. 2, 2020, will be apparent to those of ordinary skill in the art in view of the teachings herein.

In addition to the foregoing, the teachings herein may be readily combined with the teachings of U.S. patent application Ser. No. 15/634,524, entitled "Powered Surgical Instrument with Independent Selectively Applied Rotary and Linear Drivetrains," filed on Jun. 27, 2017, published as U.S. Pub. No. 2018/0368850 on Dec. 27, 2018, the disclosure of which is incorporated by reference herein. Various suitable ways in which the teachings herein may be combined with the teachings of U.S. patent application Ser. No. 15/634,524, published as U.S. Pub. No. 2018/0368850 on Dec. 27, 2018, will be apparent to those of ordinary skill in the art in view of the teachings herein.

In addition to the foregoing, the teachings herein may be readily combined with the teachings of U.S. patent application Ser. No. 15/634,556, entitled "Powered Circular Stapler with Reciprocating Drive Member to Provide Independent Stapling and Cutting of Tissue," filed on Jun. 27, 2017, published as U.S. Pub. No. 2018/0368851 on Dec. 27, 2018, the disclosure of which is incorporated by reference herein. Various suitable ways in which the teachings herein may be combined with the teachings of U.S. patent application Ser. No. 15/634,556, published as U.S. Pub. No. 2018/0368851 on Dec. 27, 2018, will be apparent to those of ordinary skill in the art in view of the teachings herein.

In addition to the foregoing, the teachings herein may be readily combined with the teachings of U.S. patent application Ser. No. 15/634,620, entitled "Surgical Stapler with Independently Actuated Drivers to Provide Varying Staple Heights," filed on Jun. 27, 2017, published as U.S. Pub. No. 2018/0368836 on Dec. 27, 2018, the disclosure of which is incorporated by reference herein. Various suitable ways in which the teachings herein may be combined with the teachings of U.S. patent application Ser. No. 15/634,620, published as U.S. Pub. No. 2018/0368836 on Dec. 27, 2018, will be apparent to those of ordinary skill in the art in view of the teachings herein.

In addition to the foregoing, the teachings herein may be readily combined with the teachings of U.S. patent application Ser. No. 15/634,589, entitled "Surgical Instrument Handle Assembly with Feature to Clean Electrical Contacts at Modular Shaft interface," filed on Jun. 27, 2017, issued as U.S. Pat. No. 10,090,616 on Oct. 2, 2018, the disclosure of which is incorporated by reference herein. Various suitable ways in which the teachings herein may be combined with the teachings of U.S. patent application Ser. No. 15/634,589, issued as U.S. Pat. No. 10,090,616 on Oct. 2, 2018, will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
 (a) a handle assembly;
 (b) a power source coupled with the handle assembly;
 (c) a control circuit coupled with the handle assembly and the power source, wherein the handle assembly, the power source, and the control circuit are configured to drive an end effector of a shaft assembly coupled with the handle assembly to perform an operation on tissue, wherein the control circuit is configured to receive life deduction event data, wherein the control circuit is configured to determine an end of life for the power source based on the life deduction event data; and
 (d) a manual input device, wherein the manual input device is configured to generate a signal, wherein the life deduction event data includes the signal generated by the manual input device, wherein the manual input device is selectively movable relative to the handle assembly between a plurality of predetermined locations, wherein each of the predetermined locations corresponds to at least one of a number of previously performed uses of the instrument, a number of remaining uses of the instrument, or a number of previously performed sterilizations of the instrument.

2. The instrument of claim 1, wherein the control circuit is configured to initiate a self-disposal mode of the power source when the power source reaches the determined end of life.

3. The instrument of claim 1, wherein the control circuit is configured to transition the instrument between a wake mode and a sleep mode, wherein the control circuit is configured to initiate a self-disposal mode of the power source when the power source reaches the determined end of life and the power source is in the sleep mode.

4. The instrument of claim 1, wherein the life deduction event data includes a type of a shaft assembly coupled with the handle assembly.

5. The instrument of claim 1, wherein the life deduction event data includes a power profile of a shaft assembly coupled with the handle assembly.

6. The instrument of claim 5, wherein the control circuit is configured to determine the power profile based at least in part on a first actuation of a user input of the handle assembly.

7. The instrument of claim 1, wherein the power source includes a battery having a voltage, wherein the control circuit is configured to monitor the voltage, wherein the life deduction event data includes the voltage of the battery.

8. The instrument of claim 1, wherein the control circuit is configured to monitor a current of the power source while the power source is in a wake mode, wherein the life deduction event data includes the current of the power source.

9. The instrument of claim 1, wherein the control circuit is configured to monitor a current of the power source while the power source is in a sleep mode, wherein the life deduction event data includes the current of the power source.

10. The instrument of claim 1, wherein the control circuit is configured to determine a number of non-use wake cycles associated with the power source, wherein the life deduction event data includes the number of non-use wake cycles.

11. The instrument of claim 1, further comprising a temperature sensor associated with the handle assembly, wherein the life deduction event data includes a temperature provided by the temperature sensor.

12. The instrument of claim 1, wherein the life deduction event data includes a shelf life associated with the power source.

13. The instrument of claim 1, wherein the control circuit is configured to determine an amount of time since the power source was coupled to the handle assembly, wherein the life deduction event data includes the amount of time.

14. The instrument of claim 1, wherein the manual input device includes a manual input clip, wherein the manual input clip is configured to generate the signal, wherein the life deduction event data includes the signal generated by the manual input clip.

15. The instrument of claim 1, wherein the manual input device includes a manual input dial, wherein the manual input dial is configured to generate the signal, wherein the life deduction event data includes the signal generated by the manual input dial.

16. The instrument of claim 1, wherein the manual input device includes a first indicia, wherein the handle assembly includes a plurality of second indicia corresponding to respective predetermined locations of the manual input device such that the first indicia is configured to selectively cooperate with each of the second indicia to provide a visual indication of at least one of the number of previously performed uses of the instrument, the number of remaining uses of the instrument, or the number of previously performed sterilizations of the instrument.

17. A method of determining an end of life for a power source of a surgical instrument, the method comprising:
  (a) coupling a power source with a handle assembly of a surgical instrument;
  (b) monitoring a life deduction event;
  (c) collecting a life deduction event data from the life deduction event;
  (d) calculating an end of life for the power source based at least in part on the life deduction event data;
  (e) determining whether a shelf life of the power source has expired;
  (f) determining whether the instrument is in a sleep mode;
  (g) initiating a self-disposal mode of the power source when the shelf life has expired and the instrument is in the sleep mode; and
  (h) generating a signal via a manual input device, wherein the life deduction event data includes the signal generated by the manual input device, wherein generating the signal includes selectively moving the manual input device relative to the handle assembly to one of a plurality of predetermined locations each corresponding to at least one of a number of previously performed uses of the instrument, a number of remaining uses of the instrument, or a number of previously performed sterilizations of the instrument.

18. The method of claim 17, further comprising:
  (a) coupling a shaft assembly to the handle assembly;
  (b) firing the handle assembly to actuate the shaft assembly; and
  (c) collecting a power drain on the power source associated with the firing of the handle assembly, wherein the life deduction event data includes the power drain on the power source associated with the firing of the handle assembly.

19. The method of claim 17, further comprising:
  (a) transforming the life deduction event data into a life debit amount;
  (b) debiting the life debit amount from a life associated with power source;
  (c) determining whether the life is beyond a disposal threshold; and
  (d) in response to determining the life is beyond the disposal threshold, initiating a self-disposal mode of the power source.

20. A method of initiating a self-disposal mode of a power source of a surgical instrument, the method comprising:
  (a) generating a signal via a manual input device, wherein generating the signal includes selectively moving the manual input device to one of a plurality of predetermined locations each corresponding to at least one of a number of previously performed uses of the instrument, a number of remaining uses of the instrument, or a number of previously performed sterilizations of the instrument;
  (b) receiving a life deduction event data, wherein the life deduction event data includes the signal generated by the manual input device;
  (c) in response to receiving the life deduction event data, calculating a life debit amount based on the life deduction event data;
  (d) debiting the life debit amount from a life associated with the power source;
  (e) determining whether the life is beyond a disposal threshold; and
  (f) in response to determining the life is beyond the disposal threshold, initiating a self-disposal mode of the power source.

* * * * *